US009719925B2

(12) United States Patent
King et al.

(10) Patent No.: US 9,719,925 B2
(45) Date of Patent: Aug. 1, 2017

(54) APPARATUS AND METHOD FOR DIFFERENTIATING MULTIPLE FLUORESCENCE SIGNALS BY EXCITATION WAVELENGTH

(71) Applicant: APPLIED BIOSYSTEMS, LLC, Carlsbad, CA (US)

(72) Inventors: Howard G. King, Berkeley, CA (US); Steven J. Boege, San Mateo, CA (US); Eugene F. Young, Marietta, GA (US); Mark F. Oldham, Emerald Hills, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 0 days.

(21) Appl. No.: 14/741,319

(22) Filed: Jun. 16, 2015

(65) Prior Publication Data

US 2015/0293024 A1    Oct. 15, 2015

Related U.S. Application Data

(63) Continuation of application No. 12/642,009, filed on Dec. 18, 2009, which is a continuation of application
(Continued)

(51) Int. Cl.
*G01N 1/00*    (2006.01)
*B01L 3/00*    (2006.01)
(Continued)

(52) U.S. Cl.
CPC ............ *G01N 21/6428* (2013.01); *B01L 7/52* (2013.01); *G01N 21/6452* (2013.01);
(Continued)

(58) Field of Classification Search
CPC ........... G01N 21/6428; G01N 21/6452; G01N 2021/6421; Y10S 435/808
See application file for complete search history.

(56) References Cited

U.S. PATENT DOCUMENTS 3,963,351 A    6/1976  Chance et al.
3,973,129 A    8/1976  Blumberg et al.
(Continued)

FOREIGN PATENT DOCUMENTS

EP    0065409    11/1982
EP    0622455    11/1994
(Continued)

OTHER PUBLICATIONS 14167180.0, "Extended European Search Report mailed Aug. 7, 2014", pp. 1-10.
(Continued)

*Primary Examiner* — Nathan Bowers

(57) ABSTRACT

An apparatus and method are provided for differentiating multiple detectable signals by excitation wavelength. The apparatus can include a light source that can emit respective excitation light wavelengths or wavelength ranges towards a sample in a sample retaining region, for example, in a well. The sample can contain two or more detectable markers, for example, fluorescent dyes, each of which can be capable of generating increased detectable emissions when excited in the presence of a target component. The detectable markers can have excitation wavelength ranges and/or emission wavelength ranges that overlap with the ranges of the other detectable markers. A detector can be arranged for detecting an emission wavelength or wavelength range emitted from a first marker within the overlapping wavelength range of at least one of the other markers.

41 Claims, 12 Drawing Sheets

Related U.S. Application Data

No. 10/440,852, filed on May 19, 2003, now Pat. No. 7,635,588.

(60) Provisional application No. 60/450,734, filed on Feb. 28, 2003, provisional application No. 60/409,152, filed on Sep. 9, 2002, provisional application No. 60/381,671, filed on May 17, 2002.

(51) Int. Cl.
    G01N 21/64 (2006.01)
    B01L 7/00 (2006.01)

(52) U.S. Cl.
    CPC .............. B01L 2300/1805 (2013.01); G01N 2021/6419 (2013.01); G01N 2021/6421 (2013.01); G01N 2021/6441 (2013.01); G01N 2201/062 (2013.01); G01N 2201/0627 (2013.01); G01N 2201/0628 (2013.01); Y10S 435/808 (2013.01)

(56) References Cited

U.S. PATENT DOCUMENTS

| | | |
|---|---|---|
| 4,284,897 A | 8/1981 | Sawamura et al. |
| 4,626,684 A | 12/1986 | Landa |
| 4,643,877 A | 2/1987 | Opitz |
| 4,673,289 A | 6/1987 | Gaucher |
| 4,683,202 A | 7/1987 | Mullis |
| 5,073,029 A | 12/1991 | Eberly et al. |
| 5,091,652 A | 2/1992 | Mathies et al. |
| 5,169,601 A | 12/1992 | Ohta et al. |
| 5,215,883 A | 6/1993 | Chu |
| 5,243,540 A | 9/1993 | Van Albert et al. |
| 5,256,880 A | 10/1993 | Loree et al. |
| 5,315,375 A | 5/1994 | Allen |
| 5,355,215 A | 10/1994 | Schroeder et al. |
| 5,371,016 A | 12/1994 | Berndt |
| 5,383,023 A | 1/1995 | Walleczek |
| 5,389,544 A | 2/1995 | Sugata et al. |
| 5,397,709 A | 3/1995 | Berndt |
| 5,475,610 A | 12/1995 | Atwood et al. |
| 5,512,758 A | 4/1996 | Kobayashi et al. |
| 5,547,849 A | 8/1996 | Baer et al. |
| 5,567,947 A | 10/1996 | Kebabian |
| 5,595,708 A | 1/1997 | Berndt |
| 5,656,493 A | 8/1997 | Mullis et al. |
| 5,672,880 A | 9/1997 | Kain |
| 5,736,333 A | 4/1998 | Livak et al. |
| 5,759,781 A | 6/1998 | Ward et al. |
| 5,766,889 A | 6/1998 | Atwood |
| 5,779,978 A | 7/1998 | Hartmann et al. |
| 5,792,610 A | 8/1998 | Witney et al. |
| 5,846,842 A | 12/1998 | Herron et al. |
| 5,854,684 A | 12/1998 | Stabile et al. |
| 5,863,502 A | 1/1999 | Southgate |
| 5,891,656 A | 4/1999 | Zarling et al. |
| 5,926,271 A | 7/1999 | Couderc et al. |
| 5,928,907 A | 7/1999 | Woudenberg et al. |
| 5,943,129 A | 8/1999 | Hoyt et al. |
| 6,040,940 A | 3/2000 | Kawasaki |
| 6,057,114 A | 5/2000 | Akong et al. |
| 6,084,667 A | 7/2000 | Melman et al. |
| 6,096,272 A | 8/2000 | Clark et al. |
| 6,121,603 A | 9/2000 | Hang et al. |
| 6,132,578 A | 10/2000 | Kambara et al. |
| 6,184,535 B1 | 2/2001 | Kashima et al. |
| 6,197,575 B1 | 3/2001 | Griffith et al. |
| 6,287,871 B1 | 9/2001 | Herron et al. |
| 6,309,601 B1 | 10/2001 | Juncosa et al. |
| 6,331,438 B1 | 12/2001 | Aylott et al. |
| 6,331,441 B1 | 12/2001 | Balch et al. |
| 6,337,740 B1 | 1/2002 | Parce |
| 6,352,672 B1 | 3/2002 | Mabile |
| 6,355,934 B1 | 3/2002 | Osgood et al. |
| 6,364,516 B1 | 4/2002 | Li et al. |
| 6,388,788 B1 | 5/2002 | Harris |
| 6,399,936 B1 | 6/2002 | Hang et al. |
| 6,411,835 B1 | 6/2002 | Modell et al. |
| 6,529,275 B2 | 3/2003 | Amirkhanian et al. |
| 6,534,011 B1 | 3/2003 | Karthe et al. |
| 6,558,624 B1 | 5/2003 | Lemmon et al. |
| 6,597,000 B2 | 7/2003 | Stern |
| 6,603,537 B1 | 8/2003 | Dietz et al. |
| 6,645,777 B1 * | 11/2003 | Letcher et al. ............... 436/526 |
| 6,743,581 B1 | 6/2004 | Vo-Dinh |
| 6,930,314 B2 | 8/2005 | Jackson et al. |
| 6,958,464 B2 | 10/2005 | Olszak et al. |
| 6,979,567 B2 | 12/2005 | Herron et al. |
| 7,635,588 B2 | 12/2009 | King |
| 2001/0033374 A1 | 10/2001 | Hoyt |
| 2002/0024026 A1 | 2/2002 | Kaushikkar |
| 2002/0055178 A1 | 5/2002 | Wardlaw |
| 2002/0060791 A1 | 5/2002 | Stumbo et al. |
| 2002/0109100 A1 | 8/2002 | Jackson et al. |
| 2002/0146688 A1 | 10/2002 | Kinjo |
| 2002/0160535 A1 | 10/2002 | Herron et al. |
| 2002/0185610 A1 | 12/2002 | Stern |
| 2003/0160182 A1 | 8/2003 | Petrich et al. |
| 2003/0230728 A1 | 12/2003 | Dai et al. |
| 2004/0086956 A1 * | 5/2004 | Bachur, Jr. ...................... 435/34 |
| 2005/0009174 A1 * | 1/2005 | Nikiforov et al. ......... 435/287.2 |
| 2010/0216143 A1 | 8/2010 | King |

FOREIGN PATENT DOCUMENTS

| | | |
|---|---|---|
| EP | 0640828 A1 | 3/1995 |
| EP | 0987539 | 3/2000 |
| EP | 1124128 | 8/2001 |
| JP | 07120392 | 5/1995 |
| JP | 07120393 | 5/1995 |
| JP | 07174701 | 7/1995 |
| JP | 09281078 | 10/1997 |
| WO | WO-9723649 | 7/1997 |
| WO | WO-97/46707 | 12/1997 |
| WO | WO-97/46708 | 12/1997 |
| WO | WO-98/57151 | 12/1998 |
| WO | WO-99/08096 | 2/1999 |
| WO | WO99/08096 | 2/1999 |
| WO | WO-99/09455 | 2/1999 |
| WO | WO99/60381 | 11/1999 |
| WO | WO-9960381 | 11/1999 |
| WO | WO-0013017 | 3/2000 |
| WO | WO-00/31518 | 6/2000 |
| WO | WO00/58715 | 10/2000 |
| WO | WO-00/58715 | 10/2000 |
| WO | WO-0058715 | 10/2000 |
| WO | WO-01/35079 | 5/2001 |
| WO | WO01/69211 | 9/2001 |
| WO | WO-01/77648 | 10/2001 |
| WO | WO-01/84463 | 11/2001 |
| WO | WO-01/96837 | 12/2001 |
| WO | WO-03/021212 | 3/2003 |
| WO | WO-03/023829 | 3/2003 |

OTHER PUBLICATIONS

Ealing, "Product catalog", 18 pages.

EP037389418, "European Search Report mailed Nov. 3, 2009", 4 pgs.

EP11193359, "European Search Report mailed Mar. 27, 2012", Mar. 27, 2012, 9 pgs.

H W Sands Corporation, "OLED Emitters Selected by Color Emission", http://www.hwsands.comlproductlists/oled/oled_emitters_color_emission.htm, Jan. 10, 2003, 5 pgs.

Hebner, T. R. et al., "Local Tuning of Organic Light-Emitting Diode Color by Dye Droplet Application American Institute of Physics.", *Applied Physics, Letters* 73, 1998, 1775-1777.

Higuchi, et al., "Real-Time Monitoring of DNA Amplification Reactions", *Kinetic PCR Analysis, Bio Technology*, vol. II, 1993, pp. 1026-1030.

(56) References Cited

OTHER PUBLICATIONS

Higuchi, R. et al., "Kinetic PCR Analysis: Real-Time Monitoring of DNA Amplification Reactions", *BioTechnology*, vol. 11, Sep. 1993, 1026-1030.

Lasercomponents.com App. Note, "http://www.lasercomponents.com/de/?embedded=1&file=fileadmin/user_upload/homeIDatasheets/omega/application-notes-filters.pdf&no_cache=1".

Omega, "Product catalog", 37 pages.

PCT/US03/15941, Notification of, and International Search Report, mailed Dec. 2, 2003, 4 pgs.

PCT/US99/011088 International Search Report mailed Sep. 15, 1999, 3 pgs.

Qiu, et al., "Room Temperature Ultraviolet Emission From an Organic Light-Emitting Diode", *American Institute of Physics*, Jul. 25, 2001, 2276-2278.

Ririe, et al., "Product Differentiation by Analysis ofDNA Melting Curves During the Polymerase Chain Reaction", *Analytical Biochemistry*, vol. 245, 1997, 154-160.

Stumbo, et al., "Light Detection Device", Publication No. US 2002/0060791 A1, May 23, 2002, 21 pgs.

Teresko, "Winning Technologies: Organic Light Emitting Diode", *Industry Week*, Dec. 11, 2000, 3 pgs.

Tollefsrud, "Organic Light Emitting Diode", http://komar.cs.stthornas.edulqm425/01sITollefsrud2.htm, Tollefsrud, Electronic Paper, Jan. 10, 2003, 5 pgs.

Wittwer, C.T. et al., "The LightCycler™: A Microvolume Multisample Fluorimeter with Rapid Temperature Control", *BioTechniques*, vol. 22 (1), Jan. 1997, 176-181.

EP16150671.2, Extended European Search Report mailed Apr. 28, 2016, 1-8.

\* cited by examiner

| | EXCITATION λ | |
| --- | --- | --- |
| | 470 | 525 |
| 5 FAM | 1.0 | 0.15 |
| TET | 0.1 | 1.0 |

APPARATUS AND METHOD FOR DIFFERENTIATING MULTIPLE FLUORESCENCE SIGNALS BY EXCITATION WAVELENGTH

CROSS-REFERENCE TO RELATED APPLICATIONS

The present application is a continuation of U.S. patent application Ser. No. 12/642,009 filed Dec. 18, 2009, which is a continuation of U.S. patent application Ser. No. 10/440,852 filed May 19, 2003, now U.S. Pat. No. 7,635,588, which claims benefit under 35 U.S.C. §119(e) from Provisional Patent Application No. 60/381,671 filed May 17, 2002, Provisional Patent Application No. 60/409,152 filed Sep. 9, 2002, and Provisional Patent Application No. 60/450,734 filed Feb. 28, 2003. All Patents, Patent Applications, and Publications mentioned herein are incorporated herein in their entireties by reference.

BACKGROUND

For identification of biological and chemical sample compositions, various quenched or unquenched dyes can be added to a sample. An unquenched dye fluoresces at a particular emission wavelength when exposed to excitation light. Quenching dyes can greatly reduces the amount of light emitted by that dye at particular wavelengths.

The apparatus and methods currently in use for sample component detection are expensive, and can require a broad spectrum of light, multiple light sources, and/or multiple detectors, for recordation and interpretation of particular emitted wavelengths from a given sample. For example, in the past, the presence of the components in a sample has been determined by detecting and differentiating specific emission wavelengths emitted from a sample, requiring relatively expensive detectors for detecting and differentiating emission wavelengths. It is desirable to create a less expensive apparatus and method of determining the composition of a sample using fluorescent dyes.

SUMMARY

An apparatus and method for differentiating multiple fluorescence signals by excitation wavelength are set forth. The apparatus and method can allow for the determination of a sample composition using specific excitation wavelengths or wavelength ranges, a plurality of detectable markers, for example, fluorescent dyes, and one or more detectors. The advent of inexpensive light sources, such as, for example, light emitting diodes (LEDs), allows the apparatus and method of the present teaching to provide multiple excitation wavelengths or wavelength ranges at a low cost, and to economically and efficiently determine the presence or absence of target components of a sample composition.

According to various embodiments, the apparatus can include a sample well and a sample arranged in the sample well. The sample can include a plurality of components including a plurality of fluorescent dyes added thereto. Each of the plurality of fluorescent dyes can exhibit an excitation wavelength range and an emission wavelength range. The emission wavelength range can overlap with an emission wavelength range of one or more of the other fluorescent dyes.

According to various embodiments, an optical instrument can be provided that includes a light source arranged to emit an excitation wavelength or wavelength range toward a region capable of retaining a sample, such that a fluorescent dye, if present in the region, can be caused to fluoresce. The light source can provide excitation wavelength ranges that correspond to respective excitation wavelength ranges of a plurality of fluorescent dyes. A detector capable of detecting an emission wavelength emitted from a fluorescing dye can be used to determine the absence or presence of a component associated with the dye. For example, the dyes can include intercalating dyes, reporter dyes, free-floating dyes, and the like.

According to various embodiments, the light source of the apparatus can be an array of light generating sources, such as an array of LEDs, lasers, or both, for example. The apparatus can further include an excitation wavelength-excluding device, an excitation wavelength focusing device, or both.

According to various embodiments, one or more of the light source and the detector can be separated from the sample by a lightpipe.

According to various embodiments, a method of differentiating multiple fluorescent signals by excitation wavelength can be provided. The method can include providing a sample including a plurality of components in a sample well and adding a plurality of fluorescent dyes to the sample. Each of the plurality of fluorescent dyes can possess a respective excitation wavelength or wavelength range and an emission wavelength or wavelength range. A respective excitation wavelength range can be directed from a light source toward the sample to excite a fluorescent dye when in the presence of a target component. Emission wavelengths that are emitted from the fluorescent dye in the sample can be detected. The presence of a particular component in the sample can be determined by the detection of a corresponding emission wavelength. The method can then be repeated utilizing different excitation wavelengths to determine the presence of other particular components in the sample. Because excitation spectra are broad, a single excitation wavelength can excite multiple dyes simultaneously. Excitation wavelengths can be chosen so as excite a first dye more strongly compared to other dyes. The other dyes can be excited weakly compared to the first dye, or not at all in the presence of the respective excitation wavelength or wavelength range. The response of each possible dye versus excitation wavelength can be measured. The response of a sample of unknown constituents can be measured. Linear algebra techniques can be used to solve a system of linear equations. The solution set thus generated can describe the concentrations of the dyes in the sample of formerly unknown constituents.

According to various embodiments, a method of differentiating multiple fluorescent signals by excitation wavelength can include multiple light sources forming excitation beams in various excitation bands. The method can include a multi-notch filter. A plurality of overlapping multi-notch filters can be utilized in the method with at least one multi-notch filter being used as an excitation filter and at least one multi-notch filter being used as an emission filter.

BRIEF DESCRIPTION OF DRAWINGS

Various embodiments of the present teachings are exemplified in the accompanying drawings. The teachings are not limited to the embodiments depicted, and include equivalent structures and methods as set forth in the following description and known to those of ordinary skill in the art. In the drawings:

FIGS. 6a-c depict several elements of various embodiments of the teachings, wherein FIG. 6a is a side view of a single sample well with a removed light source, FIG. 6b is a top view of a multiple sample well array depicting a light source and detection array, and FIG. 6c is a top view of an array of excitation wavelength excluding devices used with the light source and detection array of FIG. 6b;

It is to be understood that both the foregoing general description and the following detailed description are exemplary and explanatory only and are intended to provide a further explanation of the various embodiments of the present teachings.

DESCRIPTION

Figure 1:
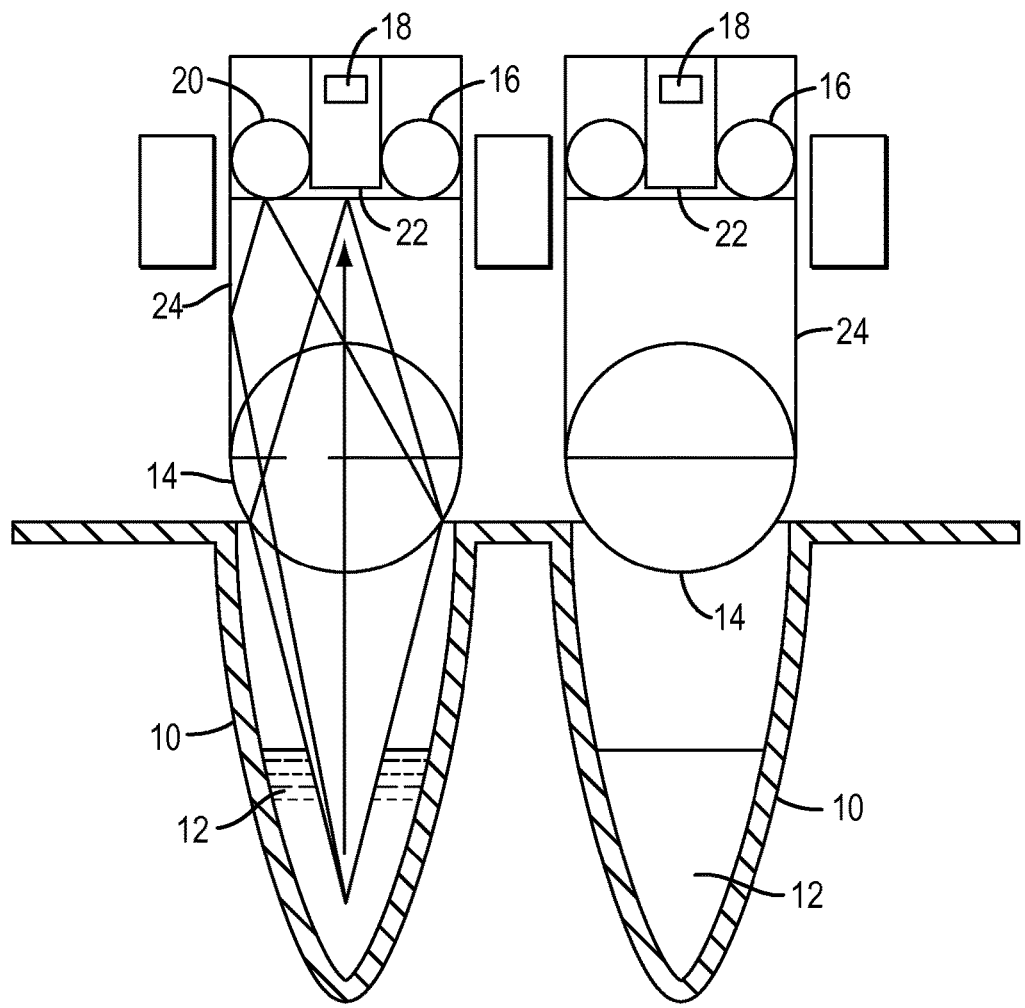
FIG. 1 depicts a side view of various embodiments.

According to various embodiments, for example, the embodiment shown in FIG. 1, an apparatus can include at least one sample well 10 adapted to receive a sample 12 containing at least two fluorescent dyes, a lens 14, a light source 16 capable of emitting at least two excitation wavelengths, and a detector 18 for detecting emission wavelengths. According to various embodiments, the apparatus can also include one or more excitation wavelength-excluding devices 22, one or more excitation wavelength-focusing devices, one or more lightpipes 24, one of more lenses 14, or combinations thereof.

According to various embodiments, the sample well 10 can be adapted to receive a sample 12 containing two or more components to be identified. For example, the sample 12 can be biological or chemical substances in solution, such as a sample containing DNA sequences for nucleic acid sequence amplification and/or sequencing detection. The sample 12 can be inserted into the sample well 10 directly, or the sample well 10 can be adapted to receive a sample container, for example, a cuvette or test tube. The sample well 10 can be a single sample well, or an array of sample wells arranged in a block, such as, for example, an array of 96 sample wells. Each sample well 10 can be heated and/or cooled during operation. Alternatively, the block can be capable of heating and cooling each sample well situated therein.

Figure 11:
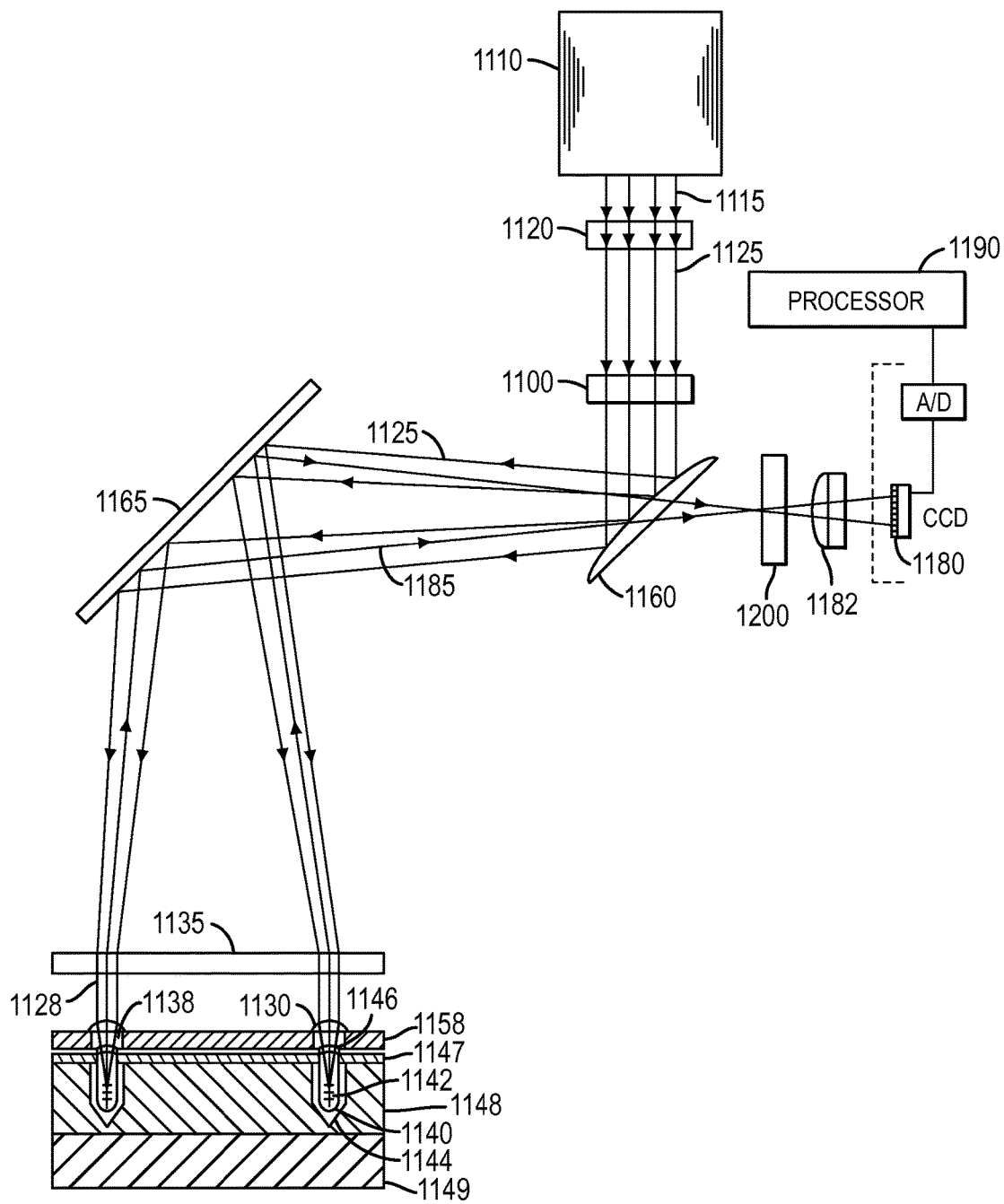
FIG. 11 is a schematic diagram of an optical instrument and an optical pathway generated by the instrument according to various embodiments.

FIG. 11 shows an exemplary instrument according to various embodiments that can include a reaction region holding assembly 1148, for example, a thermal cycler block, including wells 1144 for holding respective reaction regions 1140, for example, vials, spaced apart from one another. The reaction regions contain respective samples 1142. The samples can be, for example, respective suspensions of ingredients for polymerase chain reaction (PCR). If the reaction region holding assembly 1148 is a thermal cycler block, the assembly 1148 can include a thermal cycle controller 1149 for cycling the temperature of the block through a temperature program.

Each reaction region 1140 can include, for example, any chamber, vessel, container, sample well, capsule, vial, sample array, centrifuge tube, or other containing, restraining, retaining, or confining device, without limitation, that is capable of retaining one or more samples for fluorometric analysis or illumination thereof. The reaction regions 1140 can be fixed, secured, mounted, or otherwise attached or connected to, separate from, or integral with, the reaction region holding assembly 1148. The assembly 1148 can be attached or connected to, or placed on, a surface of a substrate or a holder and positioned to enable one or more of the reaction regions to be illuminated by a light source. The holding assembly can be, for example, a purification tray, microtiter tray, multiwell tray, sample array, micro-well array or like device for holding multiple samples.

The samples 1142 to be analyzed can include aqueous suspensions of sample materials, for example, that might include a "seed" sample of a target nucleic acid sequence, selected primers, nucleic acids, enzymes, buffers, and other chemicals conventionally used for PCR, for an isothermal reaction or another DNA amplification method well known in the art.

The reaction regions 1140 can be heated and cooled in a predetermined cycle by electric heaters, liquid or air coolants, or a combination of these, or by other methods to achieve thermal cycling. The reaction regions 1140 can be cycled between two temperature phases so as to affect PCR, for example.

According to various embodiments, two or more components of the sample 12 can be identified by adding a number of fluorescent dyes to the sample 12. Each component can be positively identified by the fluorescence of a dye.

According to various embodiments, each fluorescent dye can be selected so as to become unquenched due to the presence of a particular target component in the sample. Each fluorescent dye can be selected to possess particular excitation and emission wavelength ranges. After the dye has been added to the sample 12, a wavelength of light corresponding to the excitation wavelength range of the dye can be directed at the sample 12 by the light source 16, causing the dye to fluoresce when in the presence of a target component. The fluorescing dye can emit light at an emission wavelength that can be detected by a detector 18. Accordingly, the presence of the particular component in the sample 12 can be determined by detecting whether an emission beam at a particular wavelength or wavelength range is emitted from the sample 12 when a corresponding excitation beam is directed to the sample.

Figure 2:
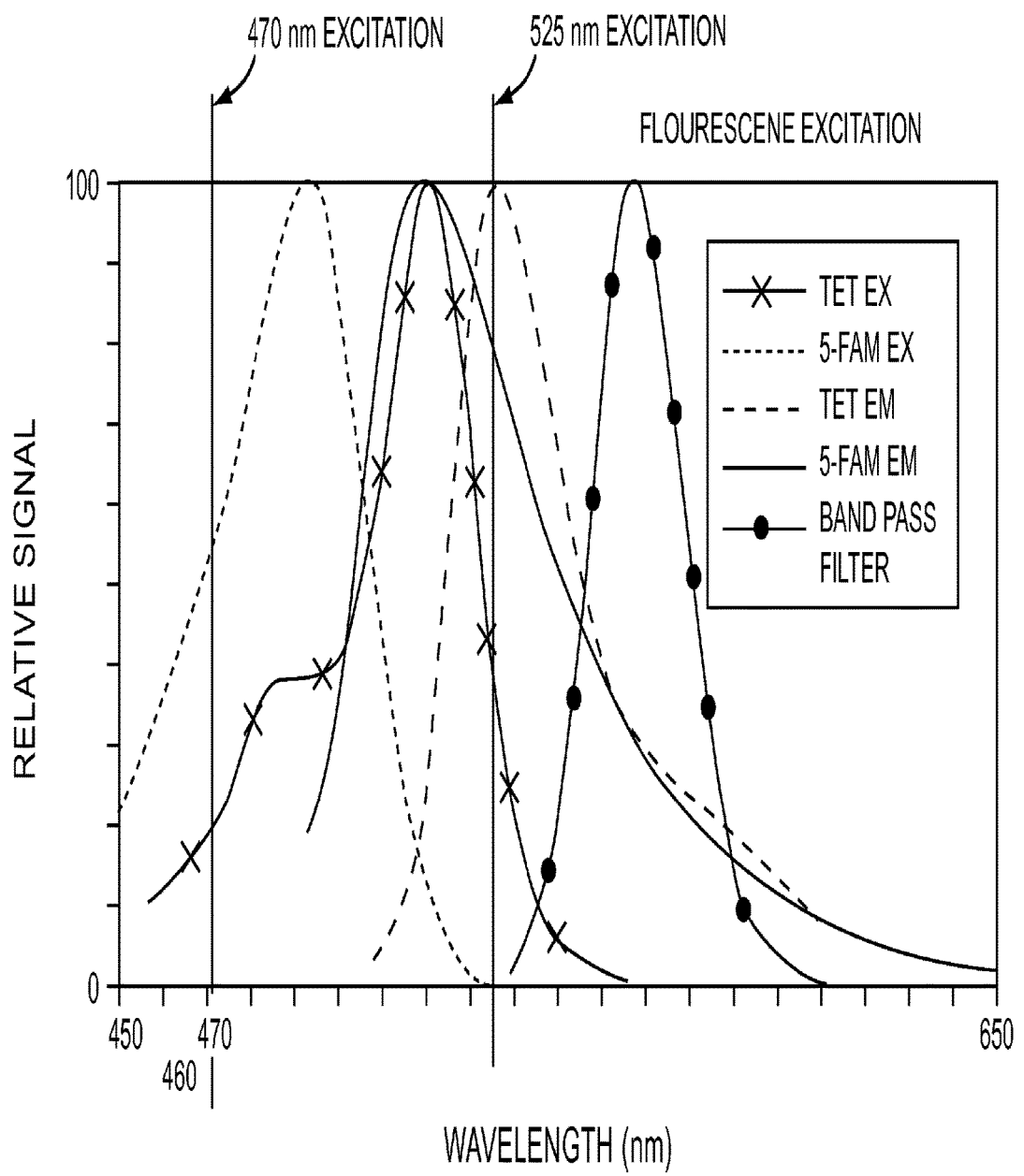
FIG. 2 is a graph showing the excitation and emission frequencies of two dyes, and the frequency of a bandpass filter for use in various embodiments.
Figures 3, 4:
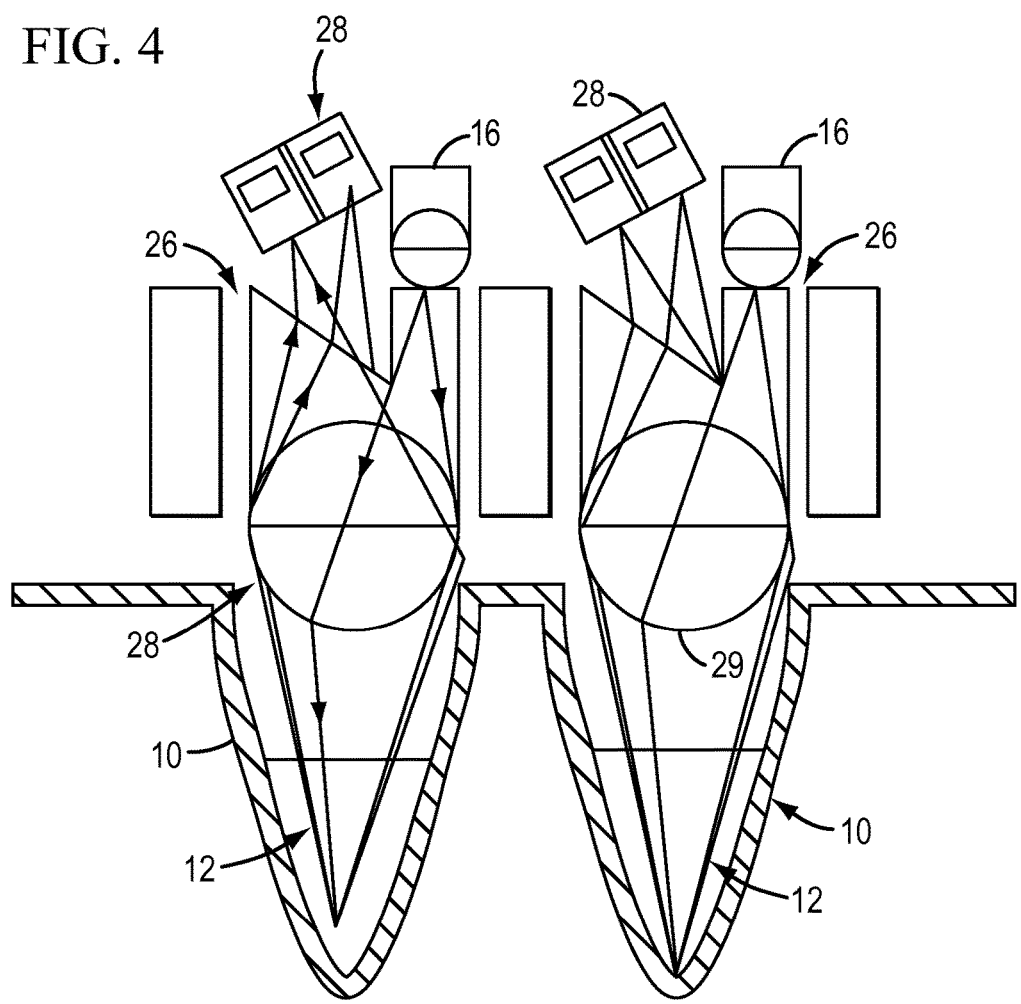
FIG. 3 is a table showing the relative amount of excitation of two dyes at two separate wavelength ranges.
FIG. 4 depicts an embodiment including a light source directed through a prism.

According to various embodiments, the presence of various dyes in a sample utilizing respective excitation wavelength ranges can be used to identify the various components. The plurality of fluorescent dyes can be chosen such that each dye possesses (a) a discrete or substantially discrete excitation wavelength range, and (b) an emission wavelength range that overlaps with an emission wavelength range of one or more of the other fluorescent dyes. For example, the excitation and emission wavelengths of exemplary dyes 5-FAM™ and TET™ are depicted in FIGS. 2 and 3. As shown, 5-FAM™ and TET™ substantially discrete excitation wavelength ranges centered at 470 nm and 525 nm, respectively. Moreover, referring to FIG. 2, within the wavelength range of approximately >600 nm, 5-FAM™ and TET™ possess substantially overlapping emission wavelengths. FIG. 2 depicts the emissions of the dyes using the following representation: TET Ex as a solid-line with x's through the line; 5-FAM Ex as a dashed-line using small dashes; TET Em as a dashed-line using long dashes; 5-FAM Em as a solid-line; and emissions after bandpass filter processing with o's through the line.

According to various embodiments, PCR dyes can be used that only fluoresce when bound to a target molecule. Nucleic acid sequence amplification dyes can also be attached to probes that also are connected to quenchers, and the action of nucleic acid sequence amplification enzymes will disassemble the dye-probe-quencher molecule causing the dye to increase its fluorescence. Nucleic acid sequence amplification can be performed using a variety of methods, for example, polymerase chain reaction (PCR), isothermal amplification reaction, well known in the art. When a PCR procedure is used, for example, the number of unquenched dye molecules doubles with every thermal cycle. Fluorescing dyes are well known in the art, and any of a plurality of fluorescent dyes having various excitation wavelengths can be used. Examples of such dyes include, but are not limited to, Rhodamine, Fluoroscein, dye derivatives of Rhodamine, dye derivatives of Fluoroscein, 5-FAM™, 6-carboxyfluorescein (6-FAM™), VIC™, hexachloro-fluorescein (HEX™), tetrachloro-fluorescein (TET™), ROX™, and TAMRA™. Dyes or other identifiers that can be used include, but are not limited to, fluorophores and phosphorescent dyes. Dyes can be used in combinations of two, three, four, or more dyes per sample. According to various embodiments, the family of 5-FAM™ 6-FAM™, VIC™, TET™, and/or ROX™ dyes can be used to indicate the presence of sample components.

According to various embodiments, there are a number of dyes that can be used in nucleic acid sequence amplification detection. The detection can be real-time. Some dyes weave themselves into the DNA and increase their fluorescence once they do. For these intercalating dyes, the fluorescence strength grows as the number of DNA molecules grows. This intercalation does not have to be sequence specific. Samples can be differentiated by looking at the DNA melting temperature. More commonly, a dye can be attached to one end of a probe DNA sequence and a quencher can be attached to the other end. When the probe binds to a target sequence, an enzyme can cleave the probe into pieces, unbinding the quencher and dye so the dyes can be excited and can release their energy via fluorescence rather than having it absorbed by the quencher. According to various embodiments, free-floating dyes can be used.

According to various embodiments, various detectable markers can be used, in addition or in alternate, to dyes. Markers can include, for example, fluorescing dyes, free-floating dyes, reporter dyes, probe dyes, intercalating dyes, and molecular beacons. Dyes that fluoresce when integrated into DNA can be intercalating dyes. Other dyes known as "reporter" dyes can attached to the ends of "probes" that have "quenchers" on the other end. A nucleic acid sequence amplification reaction, for example, PCR, can result in the disassembly of the Dye-Probe-Quencher molecule, so the reporter dye can emit an increased amount of fluorescence. Reporter dyes are not attached in any way to the sample. Free floating dyes can be floating freely in solution. Other fluorescing markers well know in the art can be utilized. According to various embodiments, molecular beacons can be single-stranded molecules with hairpins that preferentially hybridize with an amplified target to unfold.

As shown in FIGS. 1, 5, 6a, and 7, a detector 18 can be used to detect whether an emission wavelength is emitted from the sample 12. The detector can be any suitable device known in the art, including, for example, a photodiode, a charge coupled device (CCD), a camera, a CMOS detector, or any combination thereof. The detector can be adapted to relay information to a data collection device for storage, correlation, and/or manipulation of data, for example, a computer, a signal processing system.

Figure 8:
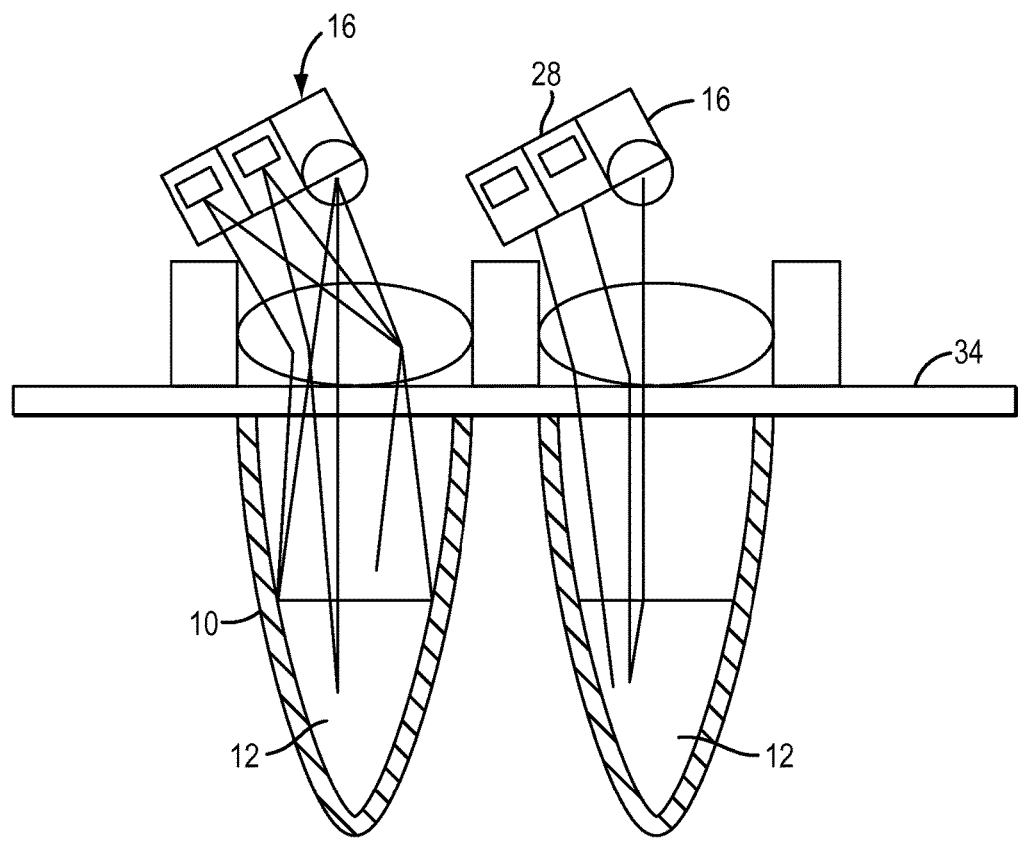
FIG. 8 depicts various embodiments wherein a light source, multiple detectors for each sample well, and a grating is used to separate the emission beam according to various wavelengths per grating diffraction.

Multiple emission detectors 28, as shown, for example, in FIGS. 4 and 8, each set to receive a respective range of wavelengths of light corresponding to the emission wavelength of particular dyes, can also be used to detect any emitted light. According to various embodiments, the multiple emission detectors 28 can be arranged as an array. Various types of multiple emission detectors for use according to various embodiments are described, for example, in Publication No. WO 01/69211 A1, which is incorporated herein in its entirety by reference.

According to various embodiments, the lens 14 can be a focusing lens that can focus a wavelength of light emitted from a light source 16 into the sample well 10. According to various embodiments, the lens 14 can focus the emission wavelength light into a detector 18, as shown, for example, in FIGS. 1, 6a, and 7.

The lens can be any suitable lens configuration, including one or more lenses. The lens can be any lens known to practitioners in the art, for example, a Fresnel lens or prism. A prism 26, as shown, for example, in FIG. 4, can be used in conjunction with a second lens 29. The prism 26 can be arranged to direct the light of the excitation beam into the sample well 10, and the second lens 29 can be arranged to focus the light of the emission beam into a detector or a detector array 28, as shown, for example, in FIG. 4. According to various embodiments, a prism 26 can be used independently without any additional lenses. According to various embodiments, articles known in the art can be arranged to direct the light, for example, a prism, a grating, a mask, of the excitation beam and/or emission beam.

According to various embodiments, the apparatus can include a light source, detector and a single lens, and can be substantially free of other optical components, for example, mirrors, beamsplitters, additional focusing lenses, etc.

According to various embodiments, the apparatus does not include a lens. According to various embodiments, the distance between the light source and sample, and the distance between the sample and detector can be proportional or thereabout to the relative distances illustrated in FIG. 5. According to various embodiments, the light source can be spaced above the sample in the range from D/2 to 5D from the top surface of the sample, where D is the depth of the sample in the well.

Figure 5:
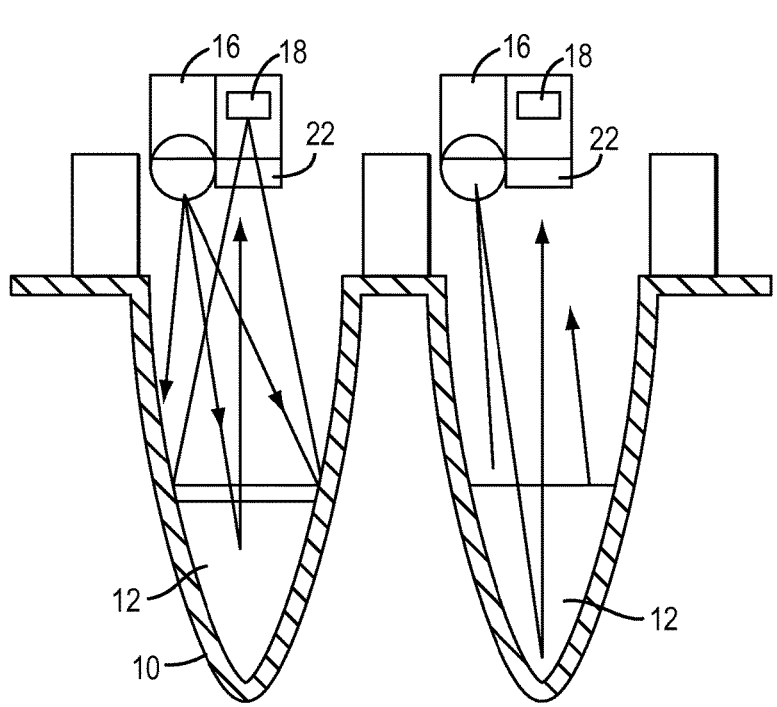
FIG. 5 depicts another embodiment of the present teachings.
Figure 6A:
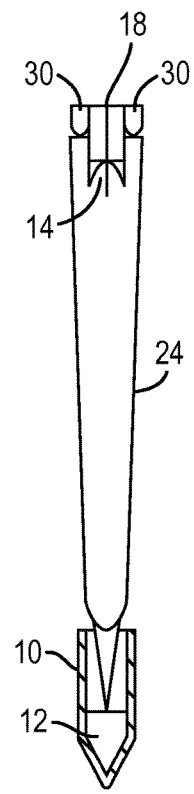
Figure 6B:
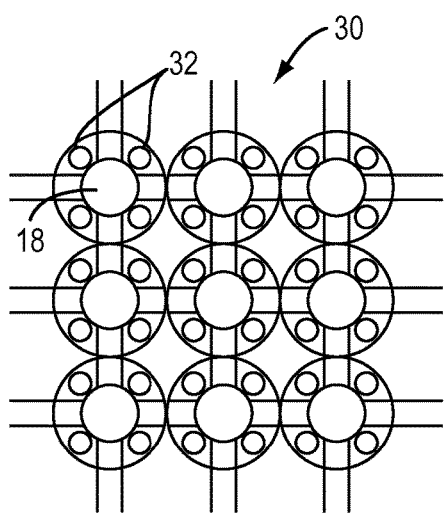

According to various embodiments, the light source 16 can include a source of light that can emit one or more respective wavelengths or wavelength ranges of light, for example, as shown in FIGS. 4 and 5, or an array 30 of two or more light sources 32, for example, as shown in FIGS. 1, 6a, and 6b.

According to various embodiments, a light array 30 includes two, three, four, or more sources of light 32 as shown, for example, in FIGS. 1, 6a and 6b. Each source of light 32 can emit a respective wavelength range of light to cause fluorescence of a different fluorescent dye. The sources of light 32 can each include any suitable light emitting device or devices that emit a narrow wavelength of light, for example, a LED, a laser, a solid state laser, a laser diode, or any combination thereof. If a laser light source is used, it can be scanned in one or more dimensions. Super bright LEDs can be used because they are inexpensive and can be arranged in a light array at low cost. According to various embodiments, separate LEDs or a packaged set of LEDs can be used in an array. Other suitable light sources will be apparent to practitioners in the art. According to various embodiments, the light source can include a combination of two, three, or more LEDs, laser diodes, and the like, such as, for example, an LED emitting at about 475 nm, an LED emitting at about 539 nm, and a photodiode emitting at about 593 nm.

According to various embodiments, the light emitted from the light source 16, such as an LED or a laser, can be divided between two samples, three samples, four samples, or more, reducing the number of light sources needed per sample well array. An exemplary multiple sample wells layout is shown, for example, in FIG. 7. The light can be divided between two or more sample wells 10 by any known device, including, for example, one or more fiber optics, flood illumination device, one more lens with or without a mask, and/or one or more beam splitter.

According to various embodiments, a broad-spectrum light source, for example, a white light or halogen light can be used as the light source 16. According to various embodiments, the emitted light of the broad-spectrum light source can be separated into distinct wavelengths or wavelength ranges such that one wavelength or wavelength range at a time can be directed toward the sample 12. The light can be divided into distinct wavelengths or wavelength ranges by an excitation wavelength focusing device, such as, for example, a prism (shown at 26 in FIG. 4), a diffraction grating (shown at 34 in FIG. 8), or a filter. The direction of a single wavelength or wavelength range can be controlled by use of an excitation wavelength-focusing device, such as, for example, a diffraction grating or filter. According to various embodiments, the broad spectrum light source can be filtered by way of a lowpass filter, for example, to prevent light in the range of emission wavelengths from reaching the sample. According to various embodiments, a pair of matching multi-notch filters can be used to prevent light in the range of emission wavelengths from reaching the sample.

According to various embodiments, the apparatus can include an excitation wavelength-excluding device 22, as shown in FIG. 1, for example. The excitation wavelength-excluding device 22 can include, for example, a diffraction grating, filter, prism, or mirror. The excitation wavelength-excluding device 22 can be positioned between the detector 18 and the sample well 10. For example, according to various embodiments, the excitation wavelength-excluding device 22 can be positioned immediately before and adjacent to a detector 18 as shown, for example, in FIGS. 1 and 7. According to various embodiments, the excitation wavelength-excluding device 22 can be a longpass filter which can transmit wavelengths greater than about 600 nm to ensure that substantially only the fluorescence emission wavelengths are received by the detector or detector array. The excitation wavelength-excluding device can be positioned between a detector and a lens, or between a lens and a sample as shown, for example, as a diffraction grating 34, in FIG. 8.

Figure 6C:
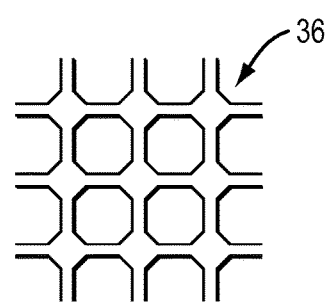
Figure 7:
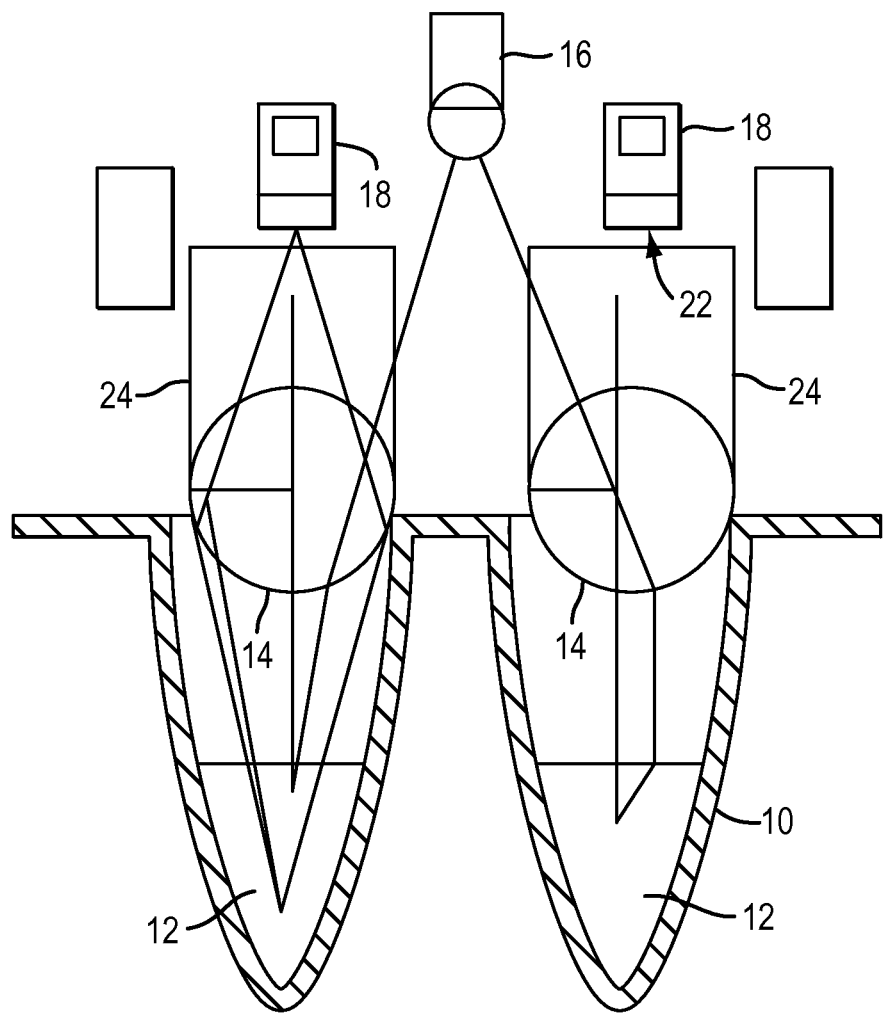
FIG. 7 depicts various embodiments having one light source emitting excitation wavelengths toward multiple sample wells, each well having a respective detector.

According to various embodiments, the excitation wavelength-excluding device can include multiple devices arranged in an array 36, as shown, for example, in FIG. 6c. According to various embodiments, the excitation wavelength-excluding device can be a prism 26 and can be positioned between the multiple emission detectors 28 and the sample 12 as shown, for example, in FIG. 4. According to various embodiments, the excitation wavelength-excluding device can be a filter. Any filter known in the art can be used, for example, a single bandpass or longpass filter.

According to various embodiments, an excitation wavelength-focusing device can be arranged to ensure that substantially only excitation wavelengths, for example, wavelengths less than about 600 nm, are impinged on the sample. The structure of these devices is as described for the excitation-wavelength excluding device. If the light source is sufficiently monochromatic, the excitation wavelength-focusing device can be omitted. According to various embodiments, the excitation wavelength-focusing device can be located between the detector and the sample well, between a detector and a lens, or between a lens and a sample well, for example.

According to various embodiments, a lightpipe 24 can be provided between the light source and the sample, and/or between the detector and the sample, as shown, for example, in FIGS. 1 and 6a. The lightpipe can be located between the light source or detector and a lens, according to various embodiments. The lightpipe 24 allows the generation of an excitation wavelength, and/or the detection of an emission wavelength, remotely from the sample well 10. The lightpipe 24 can be any suitable device for carrying wavelengths of light from one location to another without causing a significant loss of strength or shift in wavelength. According to various embodiments, such devices can include, for example, one or more fiber optic devices, mirrors, and/or lenses for transmitting the light to the sample from a remote location, and/or for transmitting the light from the sample to a remote location.

According to various embodiments, each individual light source can be provided with a light delivering light pipe 40. Each light delivery lightpipe 40 can remain separate between the light source or detector, and the sample, or each light delivery lightpipe from the light source or detector can converge to form a single lightpipe at the sample end of the lightpipe, as shown, for example, in FIG. 6a.

According to various embodiments, a method of differentiating multiple fluorescent signals by excitation wavelength can be provided. In the method, a sample 12 including a plurality of components is provided in a sample well 10. A plurality of fluorescent dyes is added to the sample 12. The plurality of fluorescent dyes can be chosen such that the emission of each fluorescent dye is greatly increased when a particular component is present in the sample 12. When the particular component is present in the sample 12, the dye can become unquenched.

Each of the plurality of detectable markers, for example, fluorescent dyes, can be selected to have an individual respective excitation wavelength or wavelength range. Each of the plurality of fluorescent dyes can be selected to possess an individual and respective emission wavelength or wavelength range. The emission wavelength or wavelength range can overlap with an emission wavelength or wavelength range of one or more of the other fluorescent dyes. A respective excitation wavelength or wavelength range is emitted from the light source 16 or 30, toward the sample 12 to fluoresce a fluorescent dye, for example, when the dye is in the presence of a target analyte in the sample 12. Emission wavelengths and wavelength ranges that are emitted from the sample 12 within the emission wavelength range of the plurality of fluorescent dyes, can be detected. The presence of a particular component in the sample 12 can be determined by the detected emission wavelength or wavelength range. The method can then be repeated utilizing different excitation wavelengths emitted from the light source 13 or 30 to determine the presence of other particular components in the sample 12.

According to various embodiments, the light source can be a Light Emitting Diode (LED). The LED can be, for example, an Organic Light Emitting Diode (OLED), a Thin Film Electroluminescent Device (TFELD), or a Quantum dot based inorganic "organic LED." The LED can include a phosphorescent OLED (PHOLED).

As used herein, the terms "excitation source" and "light source" are used interchangeably.

According to various embodiments, excitation beams emitted from the light source can diverge from the light source at an angle of divergence. The angle of divergence can be, for example, from about 5° to about 75° or more. The angle of divergence can be substantially wide, for example, greater than 45°, yet can be efficiently focused by use of a lens, such as a focusing lens.

According to various embodiments, a light source can contain one Light Emitting Diode (LED) or an array of LEDs. According to various embodiments, each LED can be a high power LED that can emit greater than or equal to about 1 mW of excitation energy. In various embodiments, a high power LED can emit at least about 5 mW of excitation energy. In various embodiments wherein the LED or array of LEDs can emit, for example, at least about 50 mW of excitation energy, a cooling device such as, but not limited to, a heat sink or fan can be used with the LED. An array of high-powered LEDs can be used that draws, for example, about 10 watts of energy or less, about 10 watts of energy or more. The total power draw can depend on the power of each LED and the number of LEDs in the array. The use of an LED array can result in a significant reduction in power requirement over other light sources, such as, for example, a 75 watt halogen light source or a 150 watt halogen light source. Exemplary LED array sources are available, for example, from Stocker Yale under the trade name LED AREALIGHTS. According to various embodiments, LED light sources can use about 1 microwatt of power or less, for example, about 1 mW, about 5 mW, about 25 mW, about 50 mW, about 1 W, about 5 W, about 50 W, or about 100 W or more, individually or when in used in an array.

According to various embodiments, a quantum dot can be used as a source for luminescence and as a fluorescent marker. The quantum dot based LED can be tuned to emit light in a tighter emission bandpass, thus the quantum dot based LED can increase the efficiency of the fluorescent system. Quantum dots can be molecular-scale optical beacons. The quantum dot nanocrystals can behave like molecular LEDs (light emitting diodes) by "lighting up" biological binding events with a broad palette of applied colors. Quantum dots can provide many more colors than conventional fluorophores. Quantum dots can possess many other very desirable optical properties. Nanocrystal quantum dots can be covalently linked to biomolecules using standard conjugation chemistry. The quantum dot conjugate can then be used to detect a binding partner in a wide range of assays. According to various embodiments, streptavidin can be attached to quantum dots to detect biotinylated molecules in a variety of assays. Quantum dots can also be attached to antibodies and oligonucleotides. Any assay that currently uses, for example, fluorescent-tagged molecules, colorimetric enzymes, or colloidal gold, can be improved with quantum dot nanocrystal-tagged conjugates. An exemplary quantum dot implementation is available from Quantum Dot Corporation of Haywood, Calif. under the trademark QDOT. More information about quantum dots and their applications can be found at, for example, www.qdot.com. U.S. Pat. Nos. 6,207,229, 6,251,303, 6,306,310, 6,319,426, 6,322,901, 6,326,144, 6,426,513, and 6,444,143 to Bawendi et al., U.S. Pat. Nos. 5,990,479, 6,207,392, and 6,423,551 to Weiss et al., U.S. Pat. No. 6,468,808 to Nie et al., and U.S. Pat. No. 6,274,323 to Bruchez et al., describe a variety of biological applications, methods of quantum dot manufacturing, and apparatuses for quantum dot nanocrystals and conjugates, all of which are incorporated herein by reference in their entireties.

Quantum dots can provide a versatile probe that can be used in, for example, in multiplex assays. Fluorescent techniques using quantum dot nanocrystals can be much faster than conventional enzymatic and chemiluminescent techniques, can reduce instrument tie-up, and can improve assay throughput. Colorimetric or detected reflectance techniques can be inferior to fluorescence and difficulties ensue when multiplex assays are developed based on these materials. Quantum dots can absorb all wavelengths "bluer" (i.e., shorter) than the emission wavelength. This capability can simplify the instrumentation required for multiplexed assays, since all different label colors can be excited with a single excitation source.

A Quantum dot based LED can emit light in an emission band that is narrower than an emission band of a normal LED, for example, about 50% narrower or about 25% narrower. The Quantum dot based LED can also emit light at an electrical energy conversion efficiency of about, 90% or more, for example, approaching 100%. OLED films, including Quantum dot based LEDs, can be applied to a thermal block, used for heating and cooling samples, in a fluorescence system without interfering with the operation of the thermal block.

According to various embodiments, when an OLED is used, the OLED can have any of a variety of sizes, shapes, wavelengths, or combinations thereof. The OLED can provide luminescence over a large area, for example, to luminescence multiple sample wells. Scatter or cross-talk light between multiple sample wells for this single OLED can be reduced by either overlaying a mask on the OLED or by patterning the luminescent in the OLED to operatively align with the multiple sample wells. The OLED can be a low power consumption device. Examples of OLEDs in various configurations and wavelengths are described in, for example, U.S. Pat. No. 6,331,438 B1, which is incorporated herein by reference in its entirety. The OLED can include a small-molecule OLED and/or a polymer-based OLED also known as a Light-Emitting Polymer (LEP). A small-molecule OLED that is deposited on a substrate can be used. An OLED that is deposited on a surface by vapor-deposition technique can be used. An OLED can be deposited on a surface by, for example, silk-screening. An LEP can be used that is deposited by, for example, solvent coating.

According to various embodiments, an OLED is used and can be formed from one or more stable, organic materials. The OLED can include one or more carbon-based thin films and the OLED can be capable of emitting light of various colors when a voltage is applied across the one or more carbon-based thin films.

According to various embodiments, the OLED can include a film that is located between two electrodes. The electrodes can be, for example, a transparent anode, a metallic cathode, or combinations thereof. Several separate emission areas can be stimulated between a single set of electrodes where simultaneous illumination of the separate emission areas is required. According to such embodiments, only one power and control module might be required for several apparent light sources. The OLED film can include one or more of a hole-injection layer, a hole-transport layer, an emissive layer, and an electron-transport layer. The OLED can include a film that is about one micrometer in thickness, or less. When an appropriate voltage is applied to the film, the injected positive and negative charges can recombine in the emissive layer to produce light by means of electroluminescence. The amount of light emitted by the OLED can be related to the voltage applied through the electrodes to the thin film of the OLED. Various materials suitable for fabrication of OLEDs are available, for example, from H.W. Sands Corp. of Jupiter, Fla. Various types of OLEDs are described, for example, in U.S. Pat. No. 4,356,429 to Tang, U.S. Pat. No. 5,554,450 to Shi et al., and U.S. Pat. No. 5,593,788 to Shi et al., all of which are incorporated herein by reference in their entireties.

According to various embodiments, an OLED can be used and produced on a flexible substrate, on an optically clear substrate, on a substrate of an unusual shape, or on a combination thereof. Multiple OLEDs can be combined on a substrate, wherein the multiple OLEDs can emit light at different wavelengths. Multiple OLEDs on a single substrate or multiple adjacent substrates can form an interlaced or a non-interlaced pattern of light of various wavelengths. The pattern can correspond to, for example, a sample reservoir arrangement. One or more OLEDs can form a shape surrounding, for example, a sample reservoir, a series of sample reservoirs, an array of a plurality of sample reservoirs, or a sample flow path. The sample path can be, for example, a channel, a capillary, or a micro-capillary. One or more OLEDs can be formed to follow the sample flow path. One or more OLEDs can be formed in the shape of a substrate or a portion of a substrate. For example, the OLED can be curved, circular, oval, rectangular, square, triangular, annular, or any other geometrically regular shape. The OLED can be formed as an irregular geometric shape. The OLED can illuminate one or more sample reservoirs, for example, an OLED can illuminate one, two, three, four, or more sample reservoirs simultaneously, or in sequence. The OLED can be designed, for example, to illuminate all the wells of a corresponding multi-well array.

According to various embodiments, one or more excitation filters can be incorporated into the OLED substrate, thus eliminating additional equipment and reducing the amount of space needed for an optical system. For example, one or more filters can be formed in a layer of a substrate including one or more OLEDs and a layer including a sample flow path. The wavelength emitted by the OLED can be tuned by printing a fluorescent dye in the OLED substrate, as taught, for example, by Hebner et al. in "Local Tuning of Organic Light-Emitting Diode Color by Dye Droplet Application," APPLIED PHYSICS LETTERS, Vol. 73, No. 13 (Sep. 28, 1998), which is incorporated herein by reference in its entirety. When using multiple emission lines in an OLED, the OLED can be used in combination with a multiple notch emission filter.

According to various embodiments, an OLED can be substituted in place of any of the systems, devices, or apparatuses where an LED is shown. The OLED light source can have several OLED films stacked and operatively disposed such that several wavelengths of excitation beams can traverse the same optical path to illuminate the sample well. Several OLEDs forming excitation beams of the same wavelength can be stacked to provide higher output to illuminate the sample well.

According to various embodiments, a sample well can be placed in between an excitation source and a detector. The sample well can be a micro card, for example, a microtiter card, such as a 96-well microtiter card. The excitation source can be, for example, an OLED, standard LED, or combination thereof.

According to various embodiments, the light source can be a Solid State Laser (SSL) or a micro-wire laser. The SSL can produce monochromatic, coherent, directional light and can provide a narrow wavelength of excitation energy. The SSL can use a lasing material that is distributed in a solid matrix, in contrast to other lasers that use a gas, dye, or semiconductor for the lasing source material. Examples of solid state lasing materials and corresponding emission wavelengths can include, for example: Ruby at about 694 nm; Nd:Yag at about 1064 nm; Nd:YVO4 at about 1064 nm and/or about 1340 nm and which can be doubled to emit at about 532 nm or about 670 nm; Alexandrite at from about 655 nm to about 815 nm; and Ti:Sapphire at from about 840 nm to about 1100 nm. Micro-wire lasers are lasers where the wavelength of an excitation beam formed by the laser can be tuned or adjusted by altering the size of a wire. According to various embodiments, other solid state lasers known to those skilled in the art can also be used, for example, laser diodes. The appropriate lasing material can be selected based on the fluorescing dyes used, the excitation wavelength required, or both.

If a SSL is used, the laser can be selected to closely match the excitation wavelength of a fluorescent dye. The operating temperature of the system can be considered in selecting an appropriate SSL. The operating temperature can be regulated or controlled to change the emitted wavelength of the SSL. The light source for the laser can be any source as known to those skilled in the art, such as, for example, a flash lamp. Useful information about various solid state lasers can be found at, for example, www.repairfaq.org/sam/lasersl.htm. Examples of solid state lasers used in various systems for identification of biological materials can be found in, for example, U.S. Pat. No. 5,863,502 to Southgate et al. and U.S. Pat. No. 6,529,275 B2 to Amirkhanian et al.; both of which are incorporated herein by reference in their entireties.

According to various embodiments, various types of light sources can be used singularly or in combination with other light sources. One or more OLEDs can be used with, for example, one or more non-organic LEDs, one or more solid state lasers, one or more halogen light sources, or combinations thereof.

According to various embodiments, a light source can be used to provide excitation beams to irradiate a sample solution containing one or more dyes. For example, two or more excitation beams having the same or different wavelength emissions can be used such that each excitation beam excites a different respective dye in the sample. The excitation beam can be aimed from the light source directly at the sample, through a wall of a sample container containing the sample, or can be conveyed by various optical systems to the sample. An optical system can include one or more of, for example, a mirror, a beam splitter, a fiber optic, a light guide, or combinations thereof.

According to various embodiments, one or more filters, for example, a bandpass filter, can be used with a light source to control the wavelength of an excitation beam. One or more filters can be used to control the wavelength of an emission beam emitted from an excited or other luminescent marker. One or more excitation filters can be associated with a light source to form the excitation beam. One or more filters can be located between the one or more light sources and a sample. One or more emission filters can be associated with an emission beam from an excited dye. One or more filters can be located between the sample and one or more emission beam detectors.

According to various embodiments, one or more filters, for example, a bandpass filter, can be used with a light source to control the wavelength of an excitation beam. One or more filters can be used to control the wavelength of an emission beam emitted from an excited or other luminescent marker. One or more excitation filters can be associated with one or more light sources to form at least one excitation beam. One or more filters can be located between the one or more light sources and a sample. One or more emission filters can be associated with an emission beam from an excited dye. One or more filters can be located between the sample and one or more emission beam detectors.

According to various embodiments, a filter can be a single bandpass filter or a multiple bandpass filter. As used herein, a bandpass filter and a passband filter are used interchangeably. A multiple passband filter can be, for example, a multiple-notch filter or a multi-rugate filter. A multiple passband filter can be used with an incoherent light source, for example, a halogen lamp, a white light source, and/or one or more LEDs or OLEDs emitting light at different wavelengths. A multiple passband filter can be used with a multiple laser-based light source emitting light at different wavelengths. Examples of manufacturing and use of rugate filters and rugate beam splitters can be found in, for example, U.S. Pat. No. 5,863,502 to Southwell, U.S. Pat. No. 6,256,148 to Gasworth, and U.S. Pat. No. 6,529,275 B2 to Rahmlow, Jr., all of which are incorporated herein by reference in their entireties.

According to various embodiments, a multiple passband filter can be used with a dichroic beam splitter, a 50/50 beam splitter, a dichroic beam splitter that has several "passbands," or no beam splitter. A multiple beam splitter can be coated at an angle, causing a variance in a thickness across a filter substrate, to compensate for wavelength shift with an angle. A multiple passband filter can be formed by coating different light interference materials over respective areas of a substrate used in a multiple passband filter manufacture.

A Rugate filter is an example of an interference coating based on the refractive index that varies continuously in a direction, for example, perpendicular or 45 degrees to the film plane. When the refractive index varies periodically within two extreme values, a minus filter with high transmittance on either side of the rejection band can be made. Periodic Rugate filters can be manufactured.

Rugate notch filters can use refractory metal oxides to achieve coatings with exceptional thermal and environmental stability. These filters can be used in place of other types of notch filters, particularly where durability and reliability are desired. Rugate notch filters are available from Ban Associates (Westford, Mass.). The Rugate notch filter can be used as edge filters and beam splitters. Filter sizes or shapes are not limitations for the rugate notch filter. The rugate notch filter can provide environmental and thermal stability, a broad operating temperature range, narrow rejection bands, variety of shapes & sizes, high throughput, low ripple, and/or a broad spectral range. More information is available from, for example, www.barr-associates-uk.com, www.barrassociates.com/opticalfilters.php.

Multiple-notch filters can be made, for example, with a measured blocking of O.D. 6 or better. Notch filters with this type of deep blocking level at the light wavelength can also afford high transmission close to the light line.

According to various embodiments, excitation levels can increase when multiple dyes spaced apart spectrally are irradiated with excitation beams. This can lead to less spectral crosstalk. The dye matrix, condition number, and/or deconvolution in a system can be improved. The increased excitation levels can provide higher signal levels. Higher signal levels can be seen during the utilization of dyes that emit in the "red" spectrum. The dynamic range of the system can be improved. The system can reduce the compensation for variation in the emission beam intensity for various dyes.

According to various embodiments, the multiple dyes can be deposited in a sample well using a fluid transfer technique, such as, for example, manual pipette, robotic pipette, or injection. According to various embodiments, the multiple dyes can be deposited in a sample well, for example, by ink-jet spraying, as beads, or as a mixture of a plurality of dyes.

Figure 9:
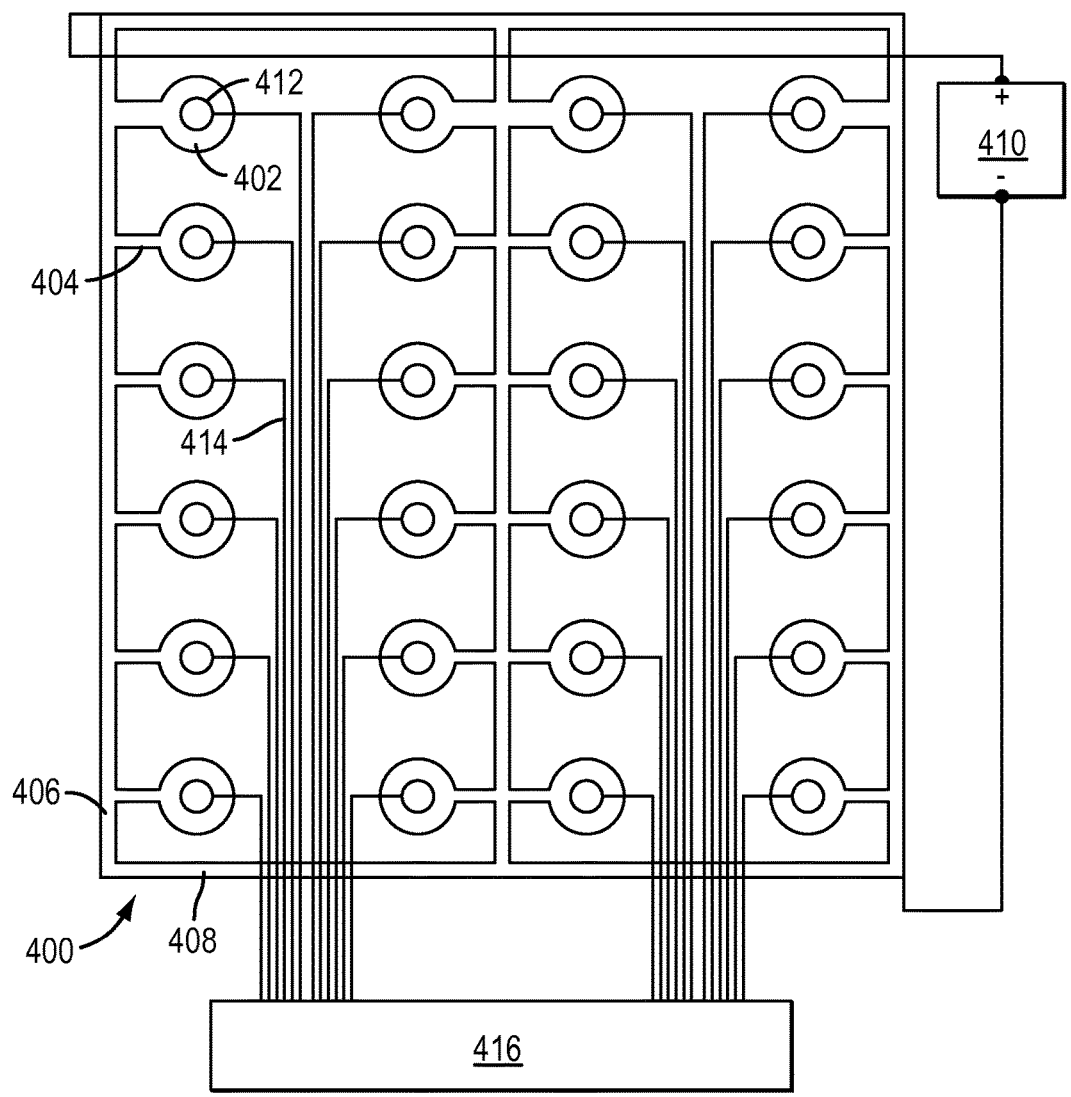
FIG. 9 illustrates an exemplary embodiment of a light source layout, for example, an organic light emitting diode (OLED) layout.

FIG. 9 is a bottom view that illustrates an OLED layout 400 that can be used as a light source, together with a plurality of photodiode detectors 412, according to various embodiments. The OLED layout 400 can include a plurality of OLED well lamps 402, each positioned, when in operation, above a respective well of a multi-well sample well array. Each OLED material well lamp 402 can be connected to, or integrally formed with, a respective connection arm 404 that leads to a layout terminal 406. Each layout terminal can be connected to or integrally formed with the respective connection arms 404 branching from the layout terminal.

The connection arms 404 branch off of side terminals 406 and 408. The OLED layout can be connected to respective opposite electrical connections, for example, opposite terminals of a power supply. The OLED layout can be connected to the power supply through leads arranged at opposite corners of the OLED layout. The power supply can include or be connected to one or more of a switch, a meter, an oscillator, a potentiometer, a detector, a signal processing unit, or the like. Alternatively, or additionally, connection arms 404 can each include a wire or electrical lead in the form of, for example, a metal wire. The OLED layout can include a plurality of individually addressable OLED lighting elements (not shown) with a separate lead connected to each lighting element. The wiring, leads, terminals, connection arms, and the like can be implemented in, for example, a substrate or a film. An OLED layout control unit 410 can be used to supply power and control the OLED layout 400.

A plurality of detectors 412 can be electrically connected to a detector control unit 416 through respective detector leads 414 as shown.

The plurality of detectors can be arranged, for example, centered, on the plurality of OLED well lamps 402, on the sides of well lamps that face respective sample wells, and/or when operatively positioned adjacent a multi-well sample well array. The detectors can be configured to detect light emitted from the sample wells of a sample well array, without being flooded or bleached out by the respective OLED well lamps. For example, a mask material can be disposed between the detectors and the respective OLED well lamps. The detector 412 can be formed in the same substrate as the OLED lamp.

The exemplary OLED layout shown in FIG. 9 is shaped to be aligned with a 24 well sample well array. Other embodiments of OLED layouts using various shapes and various numbers of well lamps are within the scope of the present teachings.

According to various embodiments, each well lamp 402 can include, for example, four individual lamps or OLED layers, capable of producing excitation wavelengths at four different frequencies.

The OLED layout can be constructed of a unitary or multi-part construction, of molded material, of stamped material, of screen printed material, of cut material, or the like.

Figure 10:
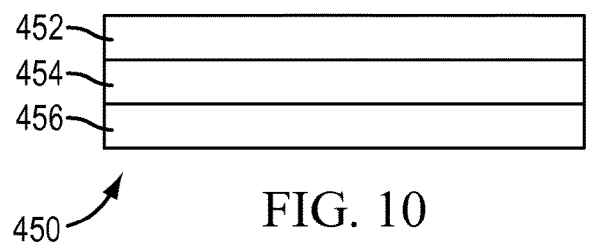
FIG. 10 illustrates an exemplary embodiment of a light source layout, for example, an OLED layout with varying color OLEDs stacked upon each other.

FIG. 10 illustrates an exemplary embodiment of a light source layout. An OLED layout 450 can include varying color OLEDs 452, 454, and 456 stacked upon each other. The layout can be useful for a compact light source design capable of forming excitation beams at varying wavelengths. The OLEDs 452, 454, and 456 can be transparent, allowing excitation beams from each OLED to pass through any other OLED so as to be directed towards a sample. The OLEDs 452, 454, and 456 can emit different colors, same colors, or a combination thereof depending on the color intensity and variety required. The OLEDs 452, 454, and 456 can share an electrode, for example, a cathode. One electrode, for example, an anode, for powering each of the OLEDs 452, 454, and 456 can be connected in electrical isolation from each respective anode to a control unit (not shown) if the capability to independently activate each of the OLEDs 452, 454, and 456 is desired. The OLEDs 452, 454, and 456 can electrically share one electrode, two electrodes, or no electrodes. Any number of OLEDs can be stacked, for example, two OLEDs, three OLEDs, four OLEDs, or more OLEDs, to form a light source, a respective light source, or an array of light sources.

Figure 12:
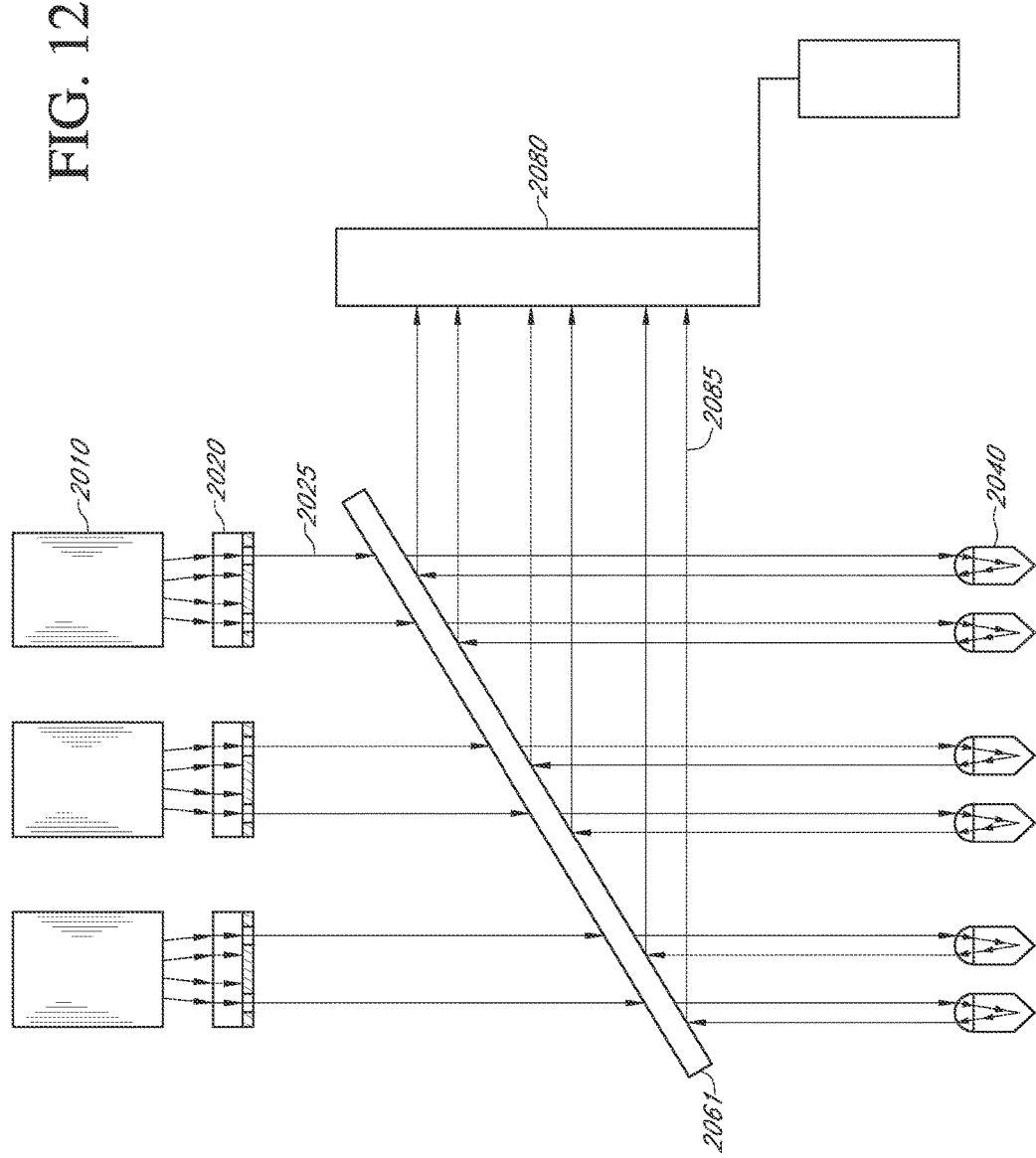
FIG. 12 is a schematic diagram of an optical instrument that includes a plurality of LEDs, a plurality of collimating lenses, a plurality of filters, a plurality of reaction region lenses, a plurality of spaced-apart reaction regions, and a detector, and the optical pathway generated by the optical instrument, according to various embodiments.
Figure 13:
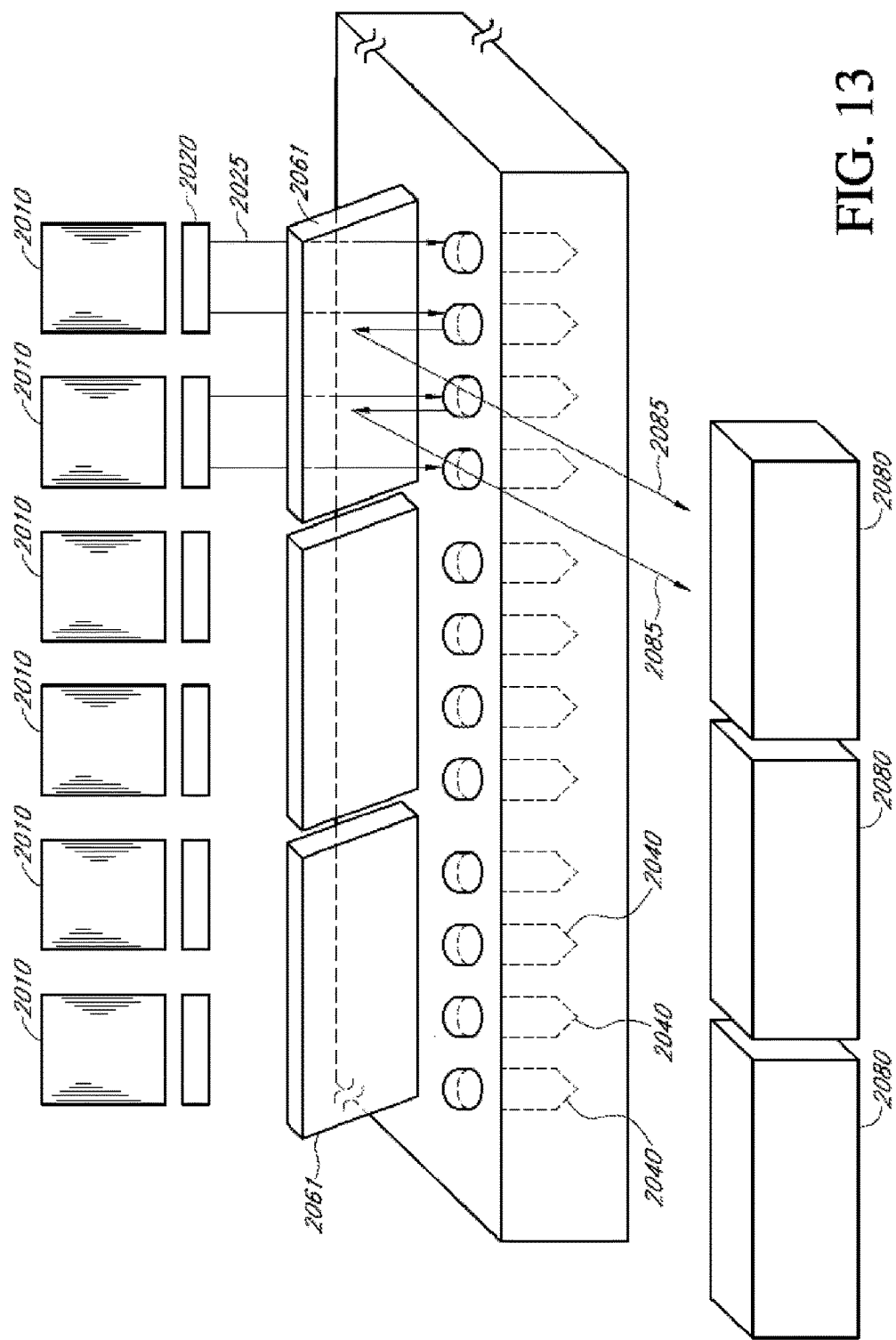
FIG. 13 is a perspective view of an optical instrument that includes a plurality of LEDs, a plurality of collimating lenses, a plurality of filters, a plurality of reaction region lenses, a plurality of spaced-apart reaction regions, and a detector, and the optical pathway generated by the optical instrument, according to various embodiments.
Figure 14:
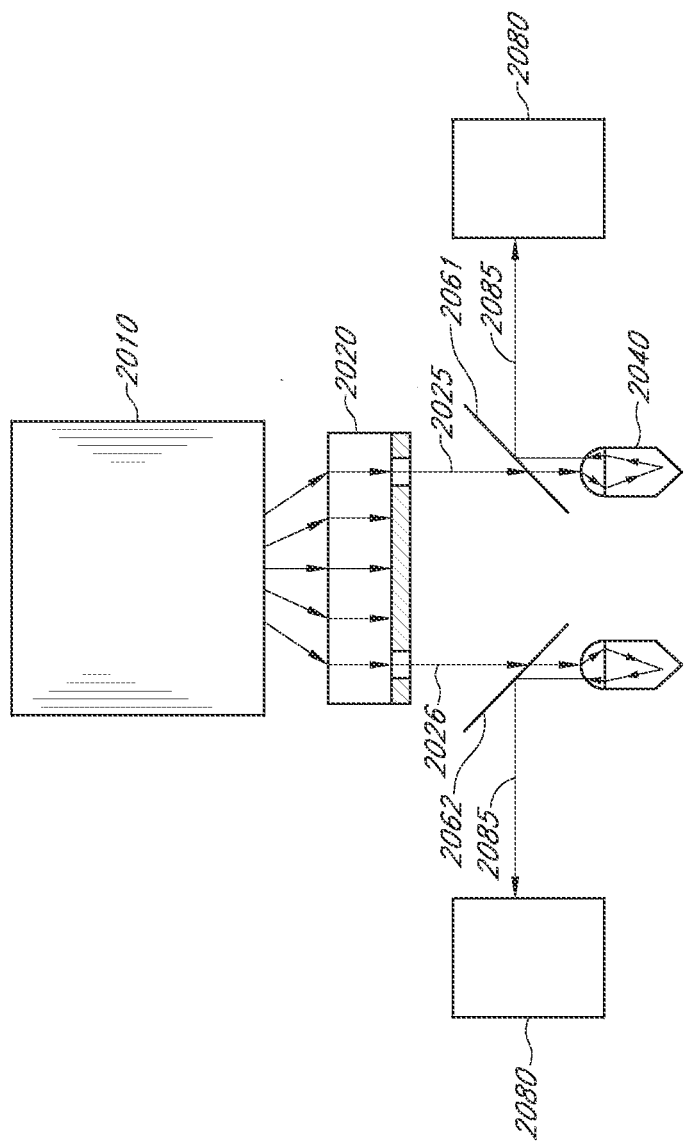
FIG. 14 is a schematic view of an optical instrument and an optical pathway generated by the optical instrument.

According to various embodiments, as shown in FIGS. 12-14, one or more transition filter 2061, 2062 such as, for example, a longpass filter, a short pass filter, a beamsplitter, a prism, or a diffraction grating, can be located between the collimating lens 2020 and the plurality of reaction regions 2040. According to various embodiments, the transition filter can be a long pass filter.

According to various embodiments, as shown in FIGS. 12-14, transition filters 2061, 2062 can pass bundles of collimated excitation beams 2025, 2026 and reflect emission beams 2085 using the exemplary arrangements shown including the LED source 2010 and detector 2080. According to various embodiments, transition filters 2061 and/or 2062 can individually be positioned at a 45° angle or at angles other than 45°. Although transition filters 2061 and 2062 can split the optical paths of the bundles of collimated excitation beams 2025, 2026 from the emission beam 2085, other variations that achieve such a result are also suitable and can be used. For example, it can be desirable to minimize or eliminate the LED source light reaching detector 2080, and a dichroic long pass filter used as transition filters 2061 and 2062 can be used to achieve this minimization. According to various embodiments, a non-dichroic long pass filter can be used for one or both of transition filters 2061 and 2062.

According to various embodiments, a transition filter can be positioned such that the filter is located along an excitation beam path between an LED source and a single reaction region. According to various other embodiments, a transition filter 2061, 2062 can be located between one or more LED source and two or more reaction regions, as shown, for example, in FIGS. 12 and 13. According to various embodiments, the transition filter 2061, 2062 can be located in an excitation beam path between a collimating lens and a focusing lens, a reaction region lens, or a reaction region. According to various embodiments, the transition filter 2061, 2062 can be located in an emission beam path between a reaction region, reaction region lens, or focusing lens, and a detector.

According to various embodiments, an LED source can emit excitation beams towards multiple reaction regions in one row of reaction regions, or in two or more rows of reaction regions. For example, each LED source in FIG. 13 can illuminate reaction regions in one row. According to various embodiments, each LED can illuminate two reaction regions in two or more adjacent rows.

According to various embodiments, the sample can contain a fluorescent dye or marker that fluoresces when unquenched in the presence of a target nucleic acid sequence to which the dye can bind. Fluorescent dye probes can be used. Other dyes that have similar characteristics can be used. The samples can also contain an additional, passive dye that can serve as a reference or control If a reference dye is included, it can include, for example, of a nucleic acid sequence labeled with a Rhodamine and/or Fluorescein dye or derivative thereof. An example of a suitable reference dye is ROX dye available from Applied Biosystems of Foster City, Calif. The passive dye molecule can be selected so as not to take part in a reaction, for example, a PCR reaction, so that fluorescence from the passive dye is substantially without influence from a target nucleic acid sequence and remains constant during the PCR. Fluorescence detected from the passive dye can be used to normalize the fluorescence from the target sequence binding dye by using a standard concentration of the passive dye in one or more of the reaction regions.

The LED source can emit excitation beams that include a secondary excitation frequency that causes the passive dye to fluoresce at a secondary emission frequency. The secondary emission frequency can be directed to a detector to generate corresponding secondary data signals. The processor can receive the secondary data signals and compute secondary data representative of the known standard concentration of the passive dye. These data can be used to normalize the primary data, so that, for example, the concentration of the target nucleic acid sequence is normalized to the standard concentration of the passive dye after correcting the concentration computations of the target sequence in proportion to adjustments made in exposure time, and in conjunction with normalization for drift, accounted for by analyzing the secondary emission frequency. Greater details about the use of passive dyes and mathematical transformations using data collected from passive dyes are set forth in the *ABI Prism* 7000 *Sequence Detection System User Guide*, pages A-1 through A-10, available from Applied Biosystems, which is incorporated herein in its entirety by reference. The secondary excitation frequency can be identical to the primary excitation frequency, and the passive dye can be selected to fluoresce such that the secondary emission frequency can be substantially at the emission frequency of the primary emission beams. In the example of PCR, the primary data signals can be generated during each extension phase of thermal cycling when the target sequence is recombined and the primary dye emission is maximized. The secondary data signals can be generated during each denature phase of thermal cycling when the target sequence is denatured and correspondingly primary dye emission is minimized. Thus, data signals for the primary phase can be substantially representative of the target sequence concentration, and data signals for the secondary phase can be substantially representative of the standard concentration of passive dye.

Suitable excitation and emission filters for use in an optical instrument can be any conventional optical bandpass filters utilizing, for example, optical interference films, each having a bandpass at a frequency that is optimal for either the excitation wavelength of the fluorescent dye or the emission wavelength of the fluorescent dye. Each filter can have very high attenuation for non-bandpass frequencies to prevent "ghost" images from being reflected and to prevent stray light. For SYBR Green dye, for example, the excitation filter bandpass can center around a 485 nm wavelength, and the emission filter bandpass can center around a 555 nm wavelength. As shown in FIGS. 12-14, transition filters 2061, 2062 can transition from reflection to transmission at a wavelength between these two, for example, at about a 510 nm wavelength, so that light of frequencies less than the transition wavelength can be reflected and higher wavelength light can pass through the filter, or vice versa. In this manner, according to various embodiments, a transition filter can function as one or more of an excitation filter and an emission filter.

Figure 15:
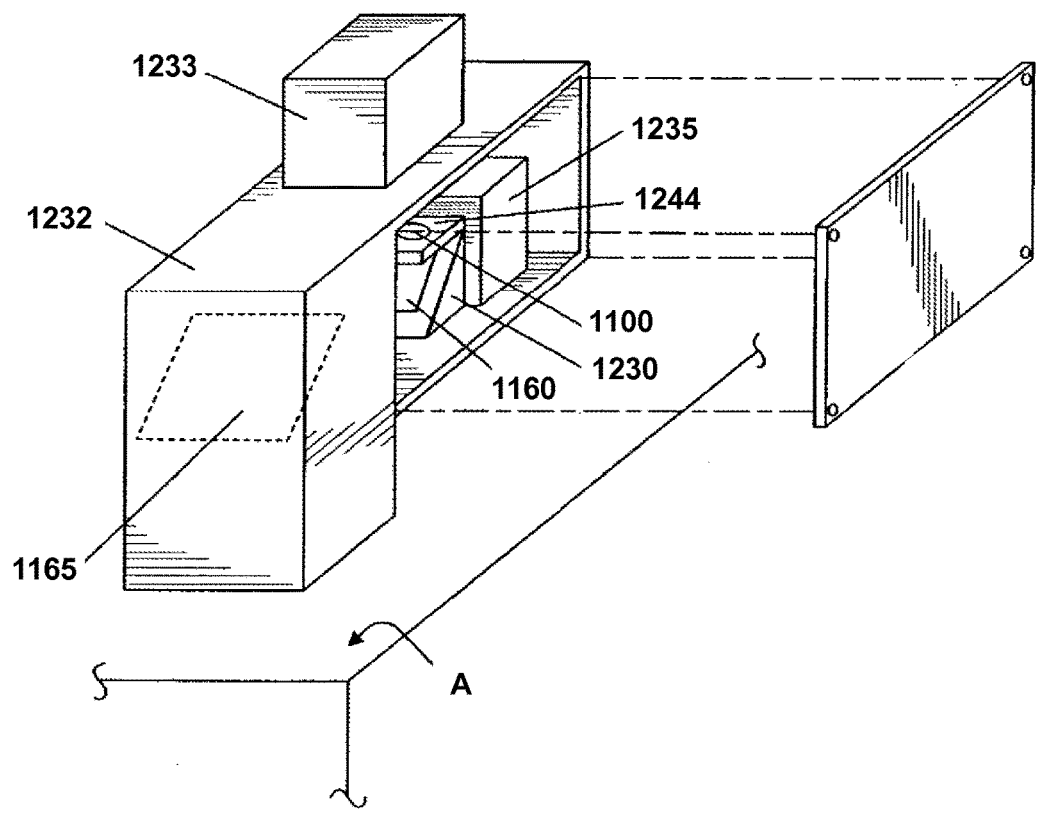
FIG. 15 is a perspective view of an optical instrument for providing the optical pathway shown in FIG. 11.

According to various embodiments, an instrument may comprise the transition filter 1160, excitation filter 1100, and emission filter 1120 affixed in a module 1230 as shown in FIG. 15. These elements can be associated with a selected primary dye used in the samples. The module can be removable from a housing 1232 of the instrument for replacement with another module capable of containing a different filter, excitation filter, and emission filter associated with another selected primary dye. The instrument can include an LED source subhousing 1233 and a detector or camera subhousing 1235. As shown in FIG. 15, the transition filter 1160 can be located in the instrument such that the transition filter 1160 is at a 45° angle with respect to a plane A of the instrument. Other suitable angles of placement of the transition filter with respect to plane A can be used.

Various embodiments of the teachings are described herein. The teachings are not limited to the specific embodiments described, but encompass equivalent features and methods as known to one of ordinary skill in the art. Other embodiments will be apparent to those skilled in the art from consideration of the present specification and practice of the teachings disclosed herein. It is intended that the present specification and examples be considered as exemplary only.

What is claimed:

1. An apparatus for measuring fluorescence, comprising:
a reaction region holding assembly configured to hold a plurality of spatially separated reaction regions each containing a respective sample; and
at least six modules, each module comprising a separate light source, the at least six modules comprising a first module, a second module, and a third module;
wherein the first module is configured to illuminate a corresponding first reaction region of the plurality of spatially separated reaction regions, the first module comprising:
a first light source characterized by a first wavelength range and configured to provide a first excitation beam directed to the first reaction region;
a first detector configured to detect a first fluorescence emission beam emitted from the first reaction region; and
a first beam splitter configured to pass the first excitation beam and reflect the first fluorescence emission beam;
wherein the second module is dispose along a first axis from the first module and is configured to illuminate a corresponding second reaction region of the plurality of spatially separated reaction regions, the second module comprising:
a second light source characterized by a second wavelength range that is different than the first wavelength range, the second light source configured to provide a second excitation beam directed to the second reaction region;
a second detector configured to detect a second fluorescence emission beam emitted from the second reaction region; and
a second beam splitter configured to pass the second excitation beam and reflect the second fluorescence emission beam; and
wherein the third module is dispose along a second axis from the first module, the second axis being orthogonal to the first axis, the third module configured to illuminate a corresponding third reaction region of the plurality of spatially separated reaction regions, the third module comprising:
a third light source configured to provide a third excitation beam directed to the third reaction region;
a third detector configured to detect a third fluorescence emission beam emitted from the third reaction region; and
a third beam splitter configured to pass the third excitation beam and reflect the third fluorescence emission beam.

2. The apparatus of claim 1, wherein the first light source is centered directly above the first reaction region and the second light source is centered directly above the second reaction region.

3. The apparatus of claim 1, wherein the detectors comprise a combination of photodiodes.

4. The apparatus of claim 1, wherein at least one of the beam splitters comprises a dichroic beam splitter.

5. The apparatus of claim 1, further comprising a microtiter plate containing the plurality of spatially separated reaction regions, wherein the reaction region holding assembly is configured to receive the microtiter plate.

6. The apparatus of claim 1, wherein the first light source and the second light source are configured during use to illuminate adjacent reaction regions of the plurality of spatially separated reaction regions.

7. The apparatus of claim 1, wherein the light sources comprise a light emitting diode emitting at about 475 nm, a light emitting diode emitting at about 539 nm, and a light emitting diode emitting at about 593 nm.

8. The apparatus of claim 1, further comprising a plurality of excitation wavelength-excluding devices, each excitation wavelength-excluding device being positioned between one of the detectors and a respective one of the reaction regions.

9. The apparatus of claim 1, wherein the excitation light sources comprises a two-dimensional array of LEDs.

10. The apparatus of claim 1, wherein the light sources are configured to simultaneously illuminate the reaction regions.

11. The apparatus of claim 1, wherein the first beam splitter, the second beam splitter, and the third beam splitter within a common plane.

12. An apparatus for measuring fluorescence, comprising:
first and second reaction regions;
a two-dimensional array of modules including at least six modules, the two-dimensional array of modules comprising:
a first module comprising:
a first light source consisting of a first LED characterized by a first wavelength range, the first light source centered directly above the first reaction region;
a first detector configured to detect a fluorescence emission emitted from a sample located within the first reaction region when the first reaction region is illuminated by the first LED; and
a first beam splitter configured to pass light within the first wavelength range and reflect the fluorescence emission from the sample located within the first reaction region;
a second module comprising:
a second light source consisting of a second LED characterized by a second wavelength range not provided by the first light source, the second light source centered directly above the second reaction region;
a second detector configured to detect a fluorescence emission emitted from a sample located within the second reaction region when the second reaction region is illuminated by the second LED; and
a second beam splitter configured to pass light within the second wavelength range and reflect the fluorescence emission from the sample located within the second reaction region; and
wherein each detector is configured to detect a fluorescence emission emitted from a reaction region that is not detected by the other detector.

13. The apparatus of claim 12, wherein the light sources are configured to simultaneously illuminate the reaction regions.

14. The apparatus of claim 12, wherein the LEDs are configured so that during operation, the first reaction region is illuminated by LED light from the first LED and the second reaction region is illuminated by LED light from the second LED.

15. The apparatus of claim 12, wherein the first and second beam splitters are disposed along a common axis.

16. The apparatus of claim 12, wherein the detectors comprise a combination of photodiodes.

17. The apparatus of claim 12, wherein at least one of the beam splitters comprises a dichroic beam splitter.

18. The apparatus of claim 12, wherein the first reaction region and the second reaction region are adjacent reaction regions.

19. The apparatus of claim 12, further comprising a microtiter plate and a plurality of spatially separated reaction regions including the first and second reaction regions, wherein the plurality of spatially separated reaction regions is configured to receive the microtiter plate.

20. The apparatus of claim 12, comprising a light emitting diode configured to emit light at about 475 nm, a light emitting diode configured to emit light at about 539 nm, and a light emitting diode configured to emit light at about 593 nm.

21. The apparatus of claim 12, further comprising a plurality of excitation wavelength-excluding devices, each excitation wavelength-excluding device being positioned between a detector and the reaction region.

22. An apparatus for measuring fluorescence, comprising:
a reaction region holding assembly configured to hold a plurality of spatially separated reaction regions each containing a respective sample; and
at least six modules, each module comprising a separate light source, the at least six modules comprising a first module, a second module, and a third module;
wherein the first module is configured to illuminate a respective first reaction region of the plurality of spatially separated reaction regions, the first module comprising:
a first light source characterized by a first wavelength range and configured to provide a first excitation beam directed to the first reaction region along a first axis between the first light source and the first reaction region;
a first detector configured to detect a first fluorescence emission emitted from the first reaction region; and
a first beam splitter configured to pass the first excitation beam and reflect the first fluorescence emission;
wherein the second module is configured to illuminate a respective second reaction region of the plurality of spatially separated reaction regions, the second module comprising:
a second light source characterized by a second wavelength range that is different than the first wavelength range, the second light source configured to provide a second excitation beam directed to the second reaction region along a second axis between the second light source and the second reaction region;
a second detector configured to detect a second fluorescence emission emitted from the second reaction region; and
a second beam splitter configured to pass the second excitation beam and reflect the second fluorescence emission, the second light source and the second beam splitter disposed along a second axis; and
wherein the third module is configured to illuminate a respective third reaction region of the plurality of spatially separated reaction regions, the third module comprising:
a third light source configured to provide a third excitation beam directed to the third reaction region along a third axis between the third light source and the third reaction region;
a third detector configured to detect a third fluorescence emission emitted from the third reaction region; and
a third beam splitter configured to pass the third excitation beam and reflect the third fluorescence emission;
wherein a plane disposed along and parallel to the first and second axes is orthogonal to a plane disposed along and parallel to the second and third axes.

23. The apparatus of claim 22, wherein the first light source is centered directly above the first reaction region and the second light source is centered directly above the second reaction region.

24. The apparatus of claim 22, wherein the detectors comprise a combination of photodiodes.

25. The apparatus of claim 22, wherein at least one of the beam splitters comprises a dichroic beam splitter.

26. The apparatus of claim 22, further comprising a microtiter plate including the plurality of spatially separated reaction regions, wherein the reaction region holding assembly is configured to receive the microtiter plate.

27. The apparatus of claim 22, wherein each light source comprises a light emitting diode.

28. The apparatus of claim 22, wherein the light sources comprise a light emitting diode emitting at about 475 nm, a light emitting diode emitting at about 539 nm, and a light emitting diode emitting at about 593 nm.

29. The apparatus of claim 22, further comprising a plurality of excitation wavelength-excluding devices, each excitation wavelength-excluding device being positioned between one of the detectors and reaction region holding assembly.

30. The apparatus of claim 22, wherein the light sources are configured to simultaneously illuminate the first reaction region and the second reaction region.

31. The apparatus of claim 22, wherein the first beam splitter, the second beam splitter, and the third beam splitter within a common plan.

32. An apparatus for measuring fluorescence, comprising:
a reaction region holding assembly configured to hold spatially separated first and second reaction regions each containing a respective sample; and
a two-dimensional array of modules including at least six modules, the two-dimensional array of modules comprising:
a first module comprising:
a first light source characterized by a first wavelength range, the first light source disposed directly above the first reaction region;
a first detector configured to detect a fluorescence emission emitted from a sample located within the first reaction region when the first reaction region is illuminated by the first LED; and
a first beam splitter configured to pass light within the first wavelength range and reflect the fluorescence emission from the sample located within the first reaction region;
a second module comprising:
a second light source characterized by a second wavelength range is different from the first wavelength range, the second light source disposed directly above the second reaction region;
a second detector configured to detect a fluorescence emission emitted from a sample located within the second reaction region when the second reaction region is illuminated by the second LED; and
a second beam splitter configured to pass light within the second wavelength range and reflect the fluorescence emission from the sample located within the second reaction region; and
wherein the first detector is configured to detect a fluorescence emission emitted from the first reaction region that is not detected by the second detector.

33. The apparatus of claim 32, wherein the first light source is centered directly above the first reaction region and the second light source is centered directly above the second reaction region.

34. The apparatus of claim 32, wherein the detectors comprise a combination of photodiodes.

35. The apparatus of claim 32, wherein at least one of the beam splitters comprises a dichroic beam splitter.

36. The apparatus of claim 32, further comprising a microtiter plate and a plurality of spatially separated reaction regions including the first and second reaction regions, wherein the plurality of spatially separated reaction regions is configured to receive the microtiter plate.

37. The apparatus of claim 32, wherein each light source comprises a light emitting diode.

38. The apparatus of claim 32, wherein the light sources comprise a light emitting diode emitting at about 475 nm, a light emitting diode emitting at about 539 nm, and a light emitting diode emitting at about 593 nm.

39. The apparatus of claim 32, further comprising a plurality of excitation wavelength-excluding devices, each excitation wavelength-excluding device being positioned between one of the detectors and a respective one of the reaction regions.

40. The apparatus of claim 32, wherein the light sources are configured to simultaneously illuminate the first reaction region and the second reaction region.

41. The apparatus of claim 32, wherein the first and second beam splitters are disposed along a common axis.

* * * * *